(12) United States Patent
Sugimoto et al.

(10) Patent No.: US 8,715,979 B2
(45) Date of Patent: *May 6, 2014

(54) METHOD OF PRODUCING FILAMENTOUS FUNGUS CULTURE PRODUCT

(75) Inventors: Toshikazu Sugimoto, Moriya (JP); Hiroshi Shoji, Moriya (JP)

(73) Assignee: Asahi Breweries, Ltd., Tokyo (JP)

( * ) Notice: Subject to any disclaimer, the term of this patent is extended or adjusted under 35 U.S.C. 154(b) by 1038 days.

This patent is subject to a terminal disclaimer.

(21) Appl. No.: 12/089,067

(22) PCT Filed: Sep. 5, 2006

(86) PCT No.: PCT/JP2006/317506
§ 371 (c)(1),
(2), (4) Date: Apr. 3, 2008

(87) PCT Pub. No.: WO2007/040008
PCT Pub. Date: Apr. 12, 2007

(65) Prior Publication Data
US 2009/0280212 A1  Nov. 12, 2009

(30) Foreign Application Priority Data

Oct. 5, 2005 (JP) ................. 2005-291876
Oct. 25, 2005 (JP) ................. 2005-309177

(51) Int. Cl.
*C12P 1/02* (2006.01)
(52) U.S. Cl.
USPC .............. 435/171; 435/41; 435/72; 435/106; 435/183; 426/7; 426/61
(58) Field of Classification Search
None
See application file for complete search history.

(56) References Cited

U.S. PATENT DOCUMENTS

| | | | |
|---|---|---|---|
| 4,358,462 A | 11/1982 | Takeda | |
| 6,051,220 A * | 4/2000 | Scharpe | 424/94.2 |
| 6,667,066 B2 | 12/2003 | Labeille et al. | |
| 6,843,994 B2 | 1/2005 | Iwasaki | |
| 2004/0082053 A1 | 4/2004 | Machida et al. | |
| 2007/0207238 A1 | 9/2007 | Sugimoto et al. | |

FOREIGN PATENT DOCUMENTS

| | | |
|---|---|---|
| EP | 1 734 109 A1 | 12/2006 |
| EP | 1 908 818 A1 | 4/2008 |
| JP | 59-140872 A | 8/1984 |
| JP | 61-293380 | 12/1986 |
| JP | 61-293380 A | 12/1986 |
| JP | 3-247265 | 11/1991 |
| JP | 3-247265 A | 11/1991 |
| JP | 7-177884 A | 7/1995 |
| JP | 8-023955 A | 1/1996 |
| JP | 10-204494 A | 8/1998 |
| JP | 11-225746 A | 8/1999 |
| JP | 2001-321154 A | 11/2001 |
| JP | 2003-47455 A | 2/2003 |
| JP | 2003-250588 A | 9/2003 |
| JP | 2003-265165 A | 9/2003 |
| JP | 2004-267065 A | 9/2004 |
| JP | 2004242532 A | 9/2004 |
| JP | 2004-290155 | 10/2004 |
| JP | 2004-290155 A | 10/2004 |
| JP | 2005-295873 | 10/2005 |
| JP | 2005295871 A | 10/2005 |
| JP | 2005-318886 | 11/2005 |
| WO | 96/11264 A1 | 4/1996 |
| WO | 2004/072280 A1 | 8/2004 |
| WO | 2005/097967 A1 | 10/2005 |
| WO | 2007/010979 A1 | 1/2007 |
| WO | 2007/039990 A1 | 4/2007 |

OTHER PUBLICATIONS

Hammes et al., Trends in Food Science and Technology, 2005, vol. 16, p. 41-11.*
Iwami et al., J Inst. Brew., 2005, vol. 111, Issue 3, p. 309-315.*
Nagamine et al., Biosci. Biotechnol. Biochem., 2003, vol. 67, No. 10, p. 2194-2202.*
Susumu Masuda, et al.; "Analysis of Enzyme Production by Submerged Culture of *Aspergillus oryzae* Using Whole Barley"; Bioscience, Biotechnology, and Biochemistry; vol. 73, No. 10; Oct. 2009; pp. 2190-2195; XP-002556619.
Hiroshi Shoji, et al.; "Simultaneous Production of Glucoamylase and Acid-Stable alpha-Amylase Using Novel Submerged Culture of *Aspergillus kawachii* NBRC4308"; Journal of Bioscience and Bioengineering; vol. 103; No. 2; Feb. 1, 2007; pp. 203-205; XP005939375.

(Continued)

*Primary Examiner* — Kade Ariani
(74) *Attorney, Agent, or Firm* — Sughrue Mion, PLLC

(57) ABSTRACT

It is an object of the present invention to provide a method of adjusting productivity of enzymes, in particular, amylolytic enzymes, plant fiber degradation enzymes and proteolytic enzymes in a filamentous fungus culture product, by controlling releasing rate of nutrients from the culture raw material into the culture system when a filamentous fungus culture product is produced by culturing filamentous fungi in liquid medium containing as the culture raw material at least one selected from the group consisting of cereals, beans, tubers, *amaranthus* and quinoa. The present invention provides a method of producing filamentous fungus culture product by using liquid medium containing as culture raw material at least one selected from the group consisting of cereals, beans, tubers, *amaranthus* and quinoa comprising, culturing filamentous fungi while releasing rate of nutrients from the culture raw material into the culture system is controlled to adjust productivity of enzymes in the filamentous fungus culture product.

5 Claims, 7 Drawing Sheets

(56) References Cited

OTHER PUBLICATIONS

Hitoshi Wadaka, et al.; "Preparation of Submerged Mold Culture Fluid for Rice Vinegar Mash"; vol. 15; Jan. 1, 1980; pp. 13-19; XP003007640.

A. Blandino, et al.; "Utilization of whole wheat flour for the production of extracellular pectinases by some fungal strains"; Process Biochemistry; vol. 37; No. 5; Dec. 20, 2001; pp. 497-503; XP003007639.

Ruohang Wang, et al.; "Protease production and conidiation by *Aspergillus oryzae* in flour fermentation"; Process Biochemistry; vol. 40; No. 1; Jan. 1, 2005; pp. 217-227.

Hisashi Fukuda, et al.; "Improvement of Material Utilization in Sake *Moromi* Brewing by Addition of Cell Wall Macerating Enzymes"; pp. 299-302; 2001; XP003007305.

Walter P. Hammes, et al.; "Microbial ecology of cereal fermentations"; Trends in Food Science & Technology; vol. 16; No. 1-3; Jan. 1, 2005; pp. 4-11; XP025324760.

Shigetoshi Sudo, et al.; "Comparison of Acid-Stable alpha-Amylase Production by *Apspergillus kawachii* in Solid-State and Submerged Cultures"; Journal of Fermentation and Bioengineering; vol. 77, No. 5; Jan. 1, 1994; pp. 483-489; 1994.

Masashi Sato, et al.; "The Effect of Polishing Rate of Rice on the Quality of Koji and Miso"; Report of the Shinshu-Miso Research Institute; 1989; XP 008115212.

Kimio Iwano, et al.; "Influence of Cultural Conditions on Various Enzyme Activities of Shochu Koji"; Journal of the Brewing Society of Japan; vol. 82, No. 3, 1987; pp. 200-204.

Masahiko Shimoda, et al., "Characteristics of water uptake of Australian polishes barley in Shochu-making", J. Inst. Brew., 1998, pp. 33-35, vol. 104, No. 1.

Hideki Narahara, et al., "Komekoji no Seikiku ni Kansuru Kenkyu", Miso Science and Technology, 1983, pp. 358-363, vol. 31, No. 9.

Kimio Iwano, et al., "Seikiku ni Okeru Genryomai no Hinshu to Seimai Buai no Eikyo", J. Brew. Soc., Japan, 2004, pp. 55-63, vol. 99, No. 1.

Hiroharu Tokuta, et al., "Koteika Itojokin ni yoru Kakushu Nama-Starch no Bunkai", The Society for Biotechnology, Japan Taikai Koen Yoshishu, 1996, p. 69, vol. 1996.

Masatoshi Goto, "Kurokojikin Glucoamylase ni yoru Nama-Starch no Bunkai", Bioscience & Industry, 2001, pp. 183-184, vol. 59, No. 3.

Keiji Kainuma, "Nama-Starch o Bunkai suru Koso", Kobunshi, 1986, p. 564, vol. 35, No. 6.

Kimio Iwano et al.; "Influence of the variety of rice and polishing rate on Japanese sake Koji making"; J. Brew. Soc. Japan, 2004, vol. 99, No. 1, pp. 55-63.

Masahiko Shimoda, et al.; "Characteristics of Water Uptake of Australian Polished Barley in Shochu-Making"; J. Inst. Brew.; Jan.-Feb. 1998; vol. 104; pp. 33-35.

Hideki Narahara, et al.; "Study on Production of Rice Koji (The Second Report) Influence Factor on Enzyme Production of *Aspergillus oryzae*"; Miso Science and Technology (1983); vol. 31, No. 9; pp. 358-363.

Hiroharu Tokuta, et al.; "Hydrolysis of Raw Starch with Immobolized Mycelia"; The Society for Biotechnology; Japan Taikai Koen Yoshisu (1996); vol. 1996; p. 69.

Masatoshi Goto; "Digestion of raw starch by glucoamylase I from *Aspergillus awamori* var. kawachi"; Bioscience & Industry (2001); vol. 59; No. 3; pp. 183-184.

Keiji Kainuma; "Special-Brewing and Synthesis—Enzymes to Degrade Raw Starch"; Kobunshi (1986); vol. 35; No. 6; p. 564.

Yuji Teramoto, et al.; "Thai ou—Characteristics of a traditional Thai alcoholic beverage drunk with a straw"; The Brewer International (2002); vol. 2; Issue 7; pp. 31-32.

Takeshi Akao, et al. "Honkaku-shochu Production Using Shaking Cultured Medium of *Aspergillus kawachii*", J. Brew. Soc. Japan, 1994, 89(11): 913-914 (with English Translation).

Annual Report from Aichi Food Research Center, 2001, The 42nd Issue (with English Translation).

Hisashi Fukuda, et al. "Improvement of Material Utilization in Sake Moromi Brewing by Addition of Cell Wall Macerating Enzymes", J. Brew. Soc. Japan, 2002, 97(12): 808-813 (with English Translation).

D.V. Gokhale, et al., "Optimization of Cellulase Production by *Aspergillus niger* NCIM 1207", Appl. Biochem. Biotechnol., 1991, 30(1): 99-109.

Yoji Hata et al., "Glucoamylase-Encoding Genes of *Aspergilllus oryzae*", Journal of the Society for Biotechnology, Japan, 2000, 78(4): 120-127 (Abstract).

"Husk" Definition from Compact Oxford English Dictionary, retrieved from http://www.askoxford.com/concise_oed/husk?view=uk, viewed Apr. 8, 2010.

Kiyoshi Ito, Progress of Aspergillus Mold Study: Molecular Genetic Analysis of Shochu Koji Molds, J. Brew. Soc., Japan, 2000, 95(9): 635-640 (with English Translation).

Taku Kato et al., "Analysis of the unique expression mode of acid-unstable a-amylase from *Aspergillus kawachii*", J. Brew. Soc., Japan, 2005, 100(7): 513-519 (Abstract).

Akitsugu Kawato, "High Production Mechanism of Glucoamylases in Solid Malt", Journal of Fushimi Joyu-kai, 1998, 13:15-25 (with English Translation).

Yojiro Koba et al., "Preparation of Koji from Corn Hulls for Alcoholic Fermentation without Cooking", J. Fement. Technol., 1986, 64(2): 175-178.

D.D. Mariani et al., "Influence of amaranth on the production of alpha-amylase using *Aspergillus neger* NRRL 3112", Rev. Argent Microbiol., 2000, 32(4): 185-189 (Abstract).

Rikke Morkeberg et al., "Induction and repression of a-amylase production in batch and continuous cultures of *Aspergillus oryzae*", Microbiology, 1995, 141(10): 2449-2454.

Wataru Nomachi et al., "Molecular Breeding of *Aspergillus kawachii* Overproducing Cellulase and Its Application to Brewing Barley Shochu", Journal of Bioscience and Bioengineering, 2002, 93(4): 382-387.

Reddy et al., "Glucose feedback inhibition of amylase activity in *Aspergillus* sp. and relase of this inhibition when cocultured with *Saccharomyces cerevisiae*", Enzyme Microbe. Technol., 1986, 8: 659-664.

Shigehisa Shibata et al., Knowledge of Flours; revised and enlarged edition, Saiwai Shobo K.K., 2000, pp. 72-73 (with English Translation).

Hiroshi Shoji et al. "Analysis of the Factor That Affect the Productivity of the Enzyme Contained in the Submerged Culture of *Apergillus kawachii* Using Whole Barley", The Society for Biotechnology Taikai Koen Yoshishu, 2006 (Mar. 8, 2006), 58: 68.

K.R. Sreekantiah et al., "Effekt of Cultural and Nutritional Variations on Certain Exo-Enzymes Secreted by Fungi", Chem. Mikrobiol. Technol. Lebensm, 1973, 2: 42-48.

Shigetoshi Sudo; "Characteristics of Acid-Stable Alpha Amylase Production by *Aspergillus kawachii*", Journal of the Brewing Society of Japan, 1994, 89: 768-774 (with English Translation).

Toshikazu Sugimoto et al., "Enzyme Production of *Aspergillus kawachii* in Submerged Cultivation Using Original Barley", The Society for Biotechnology Taikai Koen Yoshishu, 2006 (Mar. 8, 2006), 58: 69.

Ryozo Tonoike, Dictionary of Liquour, Tokyodo Syuppan K.K., 1980, pp. 79-81.

Kozo Tsuchiya et al., "High Level Secretion of Calf Chymosin Using a Glucoamylase-prochymosin Fusion Gene in *Aspergillus oryzae*", Biosci. Biotech. Biochem., 1994, 58(5): 895-899.

Poorna Viswanathan et al., "Production of a-amylase with *Aspergillus flavus* on Amaranthus grains by solid-state fermentation", J. Basic Microb. Technol., 2001, 41(1): 57-64.

Final Office Action issued Oct. 26, 2010, in U.S. Appl. No. 11/547,809 (in the name of Toshikazu Sugimoto).

Non-Final Office Action issued Mar. 15, 2011, in U.S. Appl. No. 11/995,942 (in the name of Toshikazu Sugimoto).

Final Office Action issued Jan. 4, 2011, in U.S. Appl. No. 12/067,423 (in the name of Toshikazu Sugimoto).

Final Office Action issued Sep. 30, 2010, in U.S. Appl. No. 12/090,022 (in the name of Hiroshi Shoji).

* cited by examiner (A) Glucoamylase, α-amylase (B) Acid stable α-amylase (A) Cellulase (B) β-Glucosidase

METHOD OF PRODUCING FILAMENTOUS FUNGUS CULTURE PRODUCT

CROSS REFERENCE TO RELATED APPLICATIONS

This application is a National Stage of International Application No. PCT/JP2006/317506 filed on Sep. 5, 2006, claiming priority based on Japanese Patent Application Nos. 2005-291876 and 2005-309177, filed Oct. 5, 2005 and Oct. 25, 2005, the contents of all of which are incorporated herein by reference in their entirety.

TECHNICAL FIELD

The present invention relates to a method of producing filamentous fungus culture product using liquid medium, in particular, to a method of producing filamentous fungus culture product, in which filamentous fungi are cultured while releasing rate of nutrients from the culture raw material into the culture system is controlled to adjust enzymatic productivity in the filamentous fungus culture product.

BACKGROUND ART

For producing fermented foods and drinks such as shochu, koji molds which are a kind of filamentous fungi have been used. The koji molds are cultured by the solid culture method, in which koji molds are allowed to grow on surface of cereals, that is, referred to as solid koji method. The method employing solid koji is a traditional production method. However, the method is a specific culture mode, that is, solid culture, so unsuitable for large-scale production.

On the other hand, the liquid koji, which is culture product of koji molds obtained by liquid culturing koji molds, can control culture easily, and suitable culture method for efficient production. However, it has been widely known that the liquid koji does not provide sufficient enzymatic activity required for producing fermented foods and drinks such as shochu brewing (see, Non-patent Documents 1 to 4). Therefore, there are few examples of the liquid koji being used in actual production.

In production of enzymes by liquid culturing filamentous fungi comprising koji molds, it has been known that the enzymatic productivity is improved by controlling low the concentration of nutrients such as glucose in culture system. Conventionally, the concentration of nutrients such as a saccharide has been suppressed by the feeding culture method in which nutrients such as saccharide are added little by little from outside of the culture system. However, a simpler procedure has been expected to be developed (see, Non-patent Documents 5 to 6).

We have developed a method of producing koji mold culture product containing sufficient amounts of enzymes such as glucoamylase and acid-stable α-amylase, by culturing koji molds using liquid medium in which the raw material is covered with husks or hulls, and have already filed patent applications (see, specifications of Japanese Patent Application Nos. 2004-350661, 2004-352320, 2004-352324, 2004-378453, 2005-290651, and 2005-290648). However, a mechanism how to produce the enzymes in high yields in the production method, a method how to adjust enzymatic productivity in koji mold culture product based on the mechanism, and a method how to adjust enzymatic productivity of filamentous fungi except koji molds have not been known.

On the other hand, there has been proposed a method of liquefying unboiled and unsteamed starch by using the enzyme liquid obtained by culturing, in liquid medium containing unboiled and unsteamed raw material, minerals and the like, a novel strain of genus *Corticium* which has extremely high ability of saccharifying the unboiled and unsteamed starch (see, Patent Document 1). There has also been proposed a method of producing Sake, in which the above-mentioned enzyme liquid to react with the unboiled and unsteamed raw material (see, Patent Document 2). However, the genus *Corticium* is one of bacidiomycetes, so it is significantly various from the koji molds which are widely used for producing fermented foods and drinks. In addition, Patent Document 1 and Patent Document 2 describe that a black koji mold (*Aspergillus awamori*) and genus *Rhizopus* are insufficient in saccharification abilities. It is still unclear whether the enzyme liquid has sufficient acid-stable α-amylase activity.

Non-patent Document 1: Hata Y. et. al.: J. Ferment. Bioeng., 84, 532-537 (1997)

Non-patent Document 2: Hata Y. et. al.: Gene., 207, 127-134 (1998)

Non-patent Document 3: Ishida H. et. al.: J. Ferment. Bioeng., 86, 301-307 (1998)

Non-patent Document 4: Ishida H. et. al.: Curr. Genet., 37, 373-379 (2000)

Non-patent Document 5: Bhargava S. et. al.: Biotechnol Bioeng., 82(1), 111-7 (2003)

Non-patent Document 6: Pedersen H. et. al.: Appl Microbiol Biotechnol., 53(3): 272-7 (2000)

Patent Document 1: JP H05-068237 B

Patent Document 2: JP H06-053059 B

DISCLOSURE OF THE INVENTION

Problem to be Solved by the Invention

It is an object of the present invention to provide a method of adjusting productivity of enzymes, in particular, amylolytic enzymes, plant fiber degradation enzymes and proteolytic enzymes in a filamentous fungus culture product by using liquid medium containing as culture raw material at least one selected from the group consisting of cereals, beans, tubers, *amaranthus* and quinoa, in which filamentous fungi is cultured while releasing rate of nutrients from the cereals as culture raw material into the culture system is controlled.

Means for Solving the Problem

The inventors of the present invention have made extensive studies to solve the above-mentioned problems, and as a result, have found that when the raw material covered with husks is used as raw material for liquid medium, it is possible to control liberation rate of glucose, that is one of the nutrients, into the liquid medium by adjusting polishing ratio of the raw material. As a result that filamentous fungi are cultured by using the raw materials which have various polishing ratios, it has been found that enzymatic productivity in the filamentous fungus culture product is controllable by the polishing ratio.

The inventors of the present invention also have found that koji molds are cultured in liquid medium which contains the starch-containing raw material of which husks or hulls is removed, and which is not gelatinized to produce liquid koji containing large amounts of glucoamylase and acid-stable α-amylase which are required for producing fermented foods and drinks. This is probably because the raw material which is not gelatinized hardly decomposes even not covered with husks nor hulls, whereby release of saccharide, amino acid and the like into the culture system is suppressed and, as a result, the required enzymatic activity is obtained.

The inventors of the present invention have thus completed the present invention based on those findings.

That is, according to a first aspect of the present invention, there is provided a method of producing filamentous fungus culture product by using liquid medium containing as culture raw material at least one selected from the group consisting of cereals, beans, tubers, *amaranthus* and quinoa comprising, culturing filamentous fungi while releasing rate of nutrients from the culture raw material into the culture system is controlled to adjust productivity of enzymes in the filamentous fungus culture product.

According to a second aspect of the present invention, there is provided the method of producing filamentous fungus culture product according to the first aspect of the present invention, in which the culture raw material is the cereals of which surface is entirely or partly covered with at least husks, and the releasing rate of nutrients from the cereals into the culture system is controlled by adjusting polishing ratio of the cereals.

According to a third aspect of the present invention, there is provided the method of producing filamentous fungus culture product according to the first aspect of the present invention, in which the releasing rate of nutrients from the culture raw material into the culture system is controlled by using the culture raw material of which husks or hulls are removed, and which is not gelatinized.

According to a fourth aspect of the present invention, there is provided the method of producing filamentous fungus culture product according to the first aspect of the present invention, in which the liquid medium is heat treated, and the releasing rate of nutrients from the culture raw material into the culture system is controlled by adjusting inorganic salt concentration in the liquid medium as heat treated.

According to a fifth aspect of the present invention, there is provided the method of producing filamentous fungus culture product according to the first aspect of the present invention, in which the nutrients comprise saccharide derived from starch in the culture raw material and/or amino acid derived from protein in the culture raw material.

According to a sixth aspect of the present invention, there is provided a method of producing filamentous fungus culture product according to the first aspect of the present invention, in which the enzymes comprise at least one selected from the group consisting of amylolytic enzymes, plant fiber degradation enzymes and proteolytic enzymes.

According to a seventh aspect of the present invention, there is provided the method of producing filamentous fungus culture product according to the first aspect of the present invention, in which the filamentous fungi comprise at least one selected from the group consisting of koji molds, genus *Trichoderma* and white rot fungi.

According to an eighth aspect of the present invention, there is provided a filamentous fungus culture product, which is obtained by the method according to any one of the first to seventh aspects of the present invention.

According to a ninth aspect of the present invention, there is provided a method of producing enzyme preparation comprising, using the filamentous fungus culture product according to the eighth aspect of the present invention.

According to a tenth aspect of the present invention, there is provided an enzyme preparation, which is obtained by the method according to the ninth aspect of the present invention.

According to an eleventh aspect of the present invention, there is provided a method of producing enzymes by using liquid medium containing as culture raw material at least one selected from the group consisting of cereals, beans, tubers, *amaranthus* and quinoa comprising, culturing filamentous fungi while releasing rate of nutrients from the culture raw material into the culture system is controlled to adjust productivity of enzymes in the filamentous fungus culture product.

According to a twelfth aspect of the present invention, there is provided enzymes, which are obtained by the method according to the eleventh aspect of the present invention.

According to a thirteenth aspect of the present invention, there is provided a method of producing fermented foods and drinks comprising, using the filamentous fungus culture product according to the eighth aspect of the present invention.

According to a fourteenth aspect of the present invention, there is provided a method of producing fermented foods and drinks comprising, using the enzyme preparation according to the tenth aspect of the present invention.

According to a fifteenth aspect of the present invention, there is provided a method of producing fermented foods and drinks comprising, using the enzymes according to the twelfth aspect of the present invention.

According to a sixteenth aspect of the present invention, there is provided fermented foods and drinks, which are obtained by the method according to any one of the thirteenth to fifteenth aspects of the present invention.

Effect of the Invention

According to the present invention, releasing rate of the nutrients from culture raw material into the culture system is controlled, whereby concentrations of the nutrients such as saccharide and amino acid in the culture system are maintained at low levels, and enzymatic productivity in filamentous fungus culture product is adjusted.

According to the second aspect of the present invention, liberation rate of glucose into the medium of culture system is controlled by adjusting polishing ratio. As a result of that koji mold liquid culture products are produced by using the raw materials which have various polishing ratios, it has been found that enzymatic productivity of amylolytic enzymes and plant fiber degradation enzymes is controlled by the polishing ratio. It also has been found that productivity of the enzymes produced by filamentous fungi except the koji molds is controlled by the same method.

According to the third aspect of the present invention, it is produced a filamentous fungus culture product which contains glucoamylase and acid-stable α-amylase which are required for producing fermented foods and drinks such as shochu in a balanced manner, by using the raw material which has no husks nor hulls adhered thereon.

Therefore, for example, in producing barley shochu and the like, it becomes possible to use the same raw material in the step of producing liquid koji and in the step of fermentation, whereby production cost is reduced. The hull or bran of the barley may adversely affect quality of alcohol beverages. Further, the raw material is used without being heated to save energy.

When filamentous fungus culture products are produced by combining filamentous fungus culture products obtained by using various raw materials and filamentous strains and used, it becomes possible to easily produce a variety of fermented foods and drinks.

The method of the present invention is expected to similarly control the liberation rates of many nutrients present in the cereals, such as various saccharides and amino acids, in addition to glucose. Therefore, productivity of the enzymes which is affected by catabolite repression with saccharide concentration or amino acid concentration in the culture system, would be widely adjusted.

The method of the present invention is high in possibility to apply for producing the heteroprotein which employs promoter region of an amylolytic enzyme gene and the like.

According to the present invention, concentration of nutrients such as saccharide in the medium is suppressed to low level, by adjusting liberation rate of nutrient from the raw material which has been added to the culture system in advance, even by the batch culture which is simpler than feeding culture, the culture effect same as that obtained from the feeding culture is attained. The culture method of the present invention is a novel culture mode which has not been reported before.

Further, the liquid culture is strictly controlled as compared to the solid culture. Therefore, according to the present invention, it is produced filamentous fungus culture products having stable quality at low cost.

BRIEF DESCRIPTION OF THE DRAWINGS

FIG. 3(A) shows enzymatic activities of glucoamylase (represented by white bars) and α-amylase (represented by black bars), and FIG. 3(B) shows enzymatic activities of acid-stable α-amylase.

FIG. 4(A) shows cellulase activities, and FIG. 4(B) shows β-glucosidase activities.

BEST EMBODIMENTS FOR CONDUCTING THE INVENTION

Figure 1:
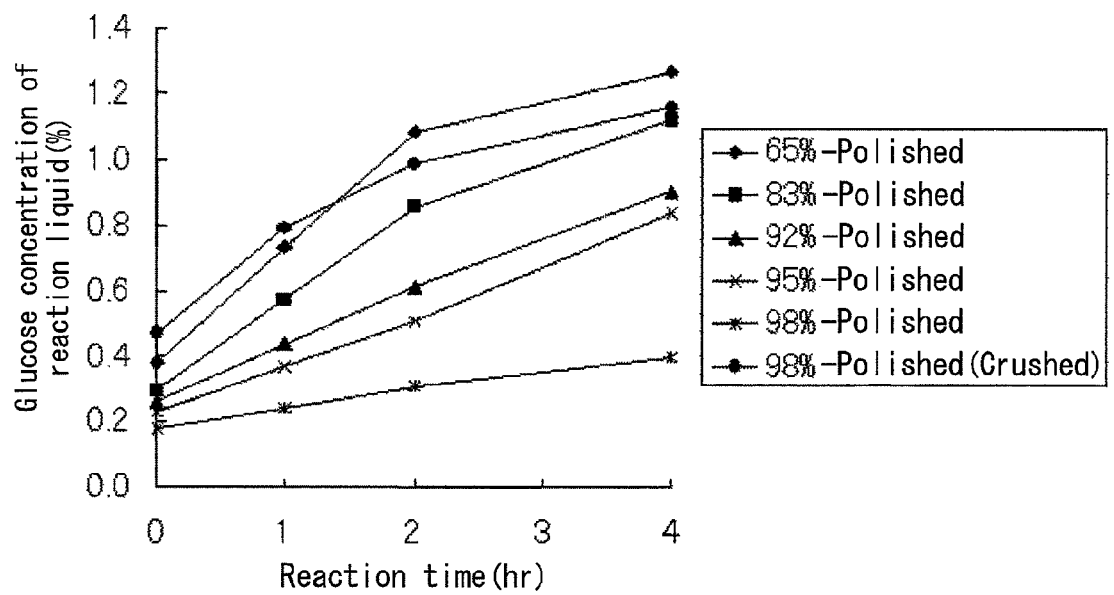
FIG. 1 shows temporal changes of glucose concentrations in reaction liquids obtained by allowing barley substrate solutions containing barley having various polishing ratios to react with koji molds culture supernatant, respectively.

Hereinafter, the present invention will be described in detail.

The first aspect of the present invention relates to a method of producing filamentous fungus culture product, characterized in that the liquid medium which contains as culture raw material at least one selected from the group consisting of cereals, beans, tubers, *amaranthus* and quinoa, and that filamentous fungi are cultured while releasing rate of nutrients from the culture raw material into the culture system is controlled to adjust productivity of enzymes in the filamentous fungus culture product.

In the present invention, the releasing rate of nutrients present in the culture raw material into the culture system is controlled, whereby concentration of the nutrients such as saccharide or amino acid which is contained in the culture system is maintained at low level, and enzymatic activity in the filamentous fungus culture product is enhanced.

Examples of means of controlling the releasing rate of nutrients in culture raw material into the culture system comprise a method by adjusting polishing ratio of cereals, a method by using as culture raw material beans, tubers, *amaranthus* or quinoa having hulls adhered thereon, a method by using the culture raw material of which husks or hulls is removed, but which is not gelatinized, a method by adjusting inorganic salt concentration as the liquid medium is heat treated, and a method by artificially forming edible film or the like on surface of the cereals to protect starch components and protein components of the cereals. However, the means are not limited thereto. The releasing rate of nutrient is controlled by suppressing physical decomposition of culture raw material in culture liquid. For instance, the releasing rate of nutrients may be suppressed by using a culture apparatus having weak stirring and shear force.

Examples of the enzyme to be produced by the filamentous fungi comprise a group of enzymes, the productivity of which is affected by catabolite repression with concentrations of saccharide such as glucose and decomposed protein such as amino acid in the culture system. Specific examples thereof comprise, but not necessarily limited to amylolytic enzymes such as glucoamylase, acid-stable α-amylase and α-amylase, plant fiber degradation enzymes such as cellulase, xylanase and β-glucosidase, and proteolytic enzymes such as protease, peptidase and glutaminase.

Examples of the culture raw material used in the present invention comprise cereals such as barley, rice, wheat, buckwheat, barnyard millet, foxtail millet, millet, kaoliang and corn, beans such as soybean and red bean, tubers such as sweet potato, and miscellaneous cereals such as *amaranthus* and quinoa.

The *amaranthus* is a generic term of plants belonging to the genus *Amaranthus* of the family Amaranthaceae. Among cereals, *amaranthus* has high protein content and the content of lysine, which is one of amino acids, is equal to that in soybean. Besides, *amaranthus* is a highly nutritious cereal containing large amounts of calcium, iron, and fibers when compared to polished rice. The countries of origin are specific areas of South/Central American countries, India, Himalayas, and Nepal.

On the other hand, the quinoa is an annual herb of Agatha family, which is mainly cultivated in highlands such as the Andes located in the southern part of Peru and the western part of Bolivia. Quinoa is rich in minerals, vitamins, proteins, and dietary fibers.

The culture raw materials may be used alone, or two or more of them may be used in combination. The shape of the raw materials is not particularly limited.

Any one of the culture raw materials is mixed with water to prepare liquid medium.

Blending ratios of the culture raw materials are each adjusted to the extent that the enzymes intended to be accumulated are selectively produced and accumulated in the filamentous fungus culture product.

For instance, in order to produce glucoamylase and acid-stable α-amylase in high yields in a balanced manner, when barley is used as raw material, liquid medium is prepared by adding 1 to 20% (w/vol) of crude barley to water. When unpolished barley is used as crude barley, liquid medium is prepared with the addition of more preferably 8 to 10% (w/vol). When 95%-polished barley as crude barley is used as raw material, liquid medium is prepared with the addition of more preferably 1 to 4% (w/vol).

When the amount of the crude barley to be used exceeds 20% (w/vol), viscosity of the culture liquid increases and supply of oxygen or air required for aerobically culturing filamentous fungi becomes insufficient. That decreases oxygen content in the culture product, restricts culture progress, and is not preferred.

Next, when rice is used as culture raw material, liquid medium is prepared by adding 1 to 20% (w/vol), preferably 5 to 13% (w/vol), or more preferably 8 to 10% (w/vol) of rice to water.

When beans are used as culture raw material, liquid medium is prepared by adding 1 to 10% (w/vol) of beans to water, or preferably, by adding 8 to 10% (w/vol) of soybean or 1 to 2% (w/vol) of red bean to water. When tuber is used as culture raw material, liquid medium is prepared by adding 1 to 10% (w/vol) of tuber to water.

When *amaranthus* is used as culture raw material, for example, liquid medium is prepared by adding 1.5 to 15% (w/vol), preferably 2 to 10% (w/vol), or more preferably 2 to 8% (w/vol) of *amaranthus* to water. When quinoa is used as culture raw material, liquid medium is prepared by adding 1.5 to 7% (w/vol), preferably 2 to 6% (w/vol), or more preferably 2 to 4% (w/vol) of quinoa to water.

The amounts of the culture raw materials to be blended may appropriately be selected because the amounts most suitable for the blending vary dependent on the intended enzymes, polishing degrees of the raw materials to be used, the filamentous strain to be used, the kinds of the raw materials and the like.

In addition to any one of the above-mentioned raw materials, it is preferable that organic substances, inorganic salts and the like are added as nutrient source to the liquid medium.

For instance, when white koji molds such as *Aspergillus kawachii* and black koji molds such as *Aspergillus awamori* or *Aspergillus niger* are used as the filamentous fungi, nitrate salts and phosphate salts are preferably used in combination, or more preferably, sulfate salts is used in combination in addition to them. Examples of the nitrate salts comprise sodium nitrate and potassium nitrate, and potassium nitrate is particularly preferable. Examples of the phosphate salts comprise potassium dihydrogen phosphate and ammonium phosphate, and potassium dihydrogen phosphate is particularly preferable. Examples of the sulfate salts comprise magnesium sulfate heptahydrate, iron sulfate heptahydrate and ammonium sulfate, and magnesium sulfate heptahydrate and iron sulfate heptahydrate are particularly preferable. Two or more of those inorganic salts may be used in combination.

Concentrations of the inorganic salts in liquid medium when the white koji and black koji are used are each adjusted to the extent that glucoamylase and α-amylase are selectively generated and accumulated in the koji mold culture product. To be specific, the concentration of nitrate salts is 0.1 to 2.0%, or preferably 0.2 to 1.5%, the concentration of phosphate salts is 0.05 to 1.0%, or preferably 0.1 to 0.5%, and the concentration of sulfate salts is 0.01 to 0.5%, or preferably 0.02 to 0.1%, provided that, every value is in w/vol.

When yellow koji molds such as *Aspergillus oryzae* or *Aspergillus sojae* are used as the filamentous fungus, liquid medium preferably contains nitrate salts, phosphate salts and sulfate salts in combination. Examples of the nitrate salts comprise sodium nitrate and potassium nitrate, and sodium nitrate is particularly preferable. Examples of the phosphate salts comprise potassium dihydrogen phosphate and ammonium phosphate, and potassium dihydrogen phosphate is particularly preferable. Examples of the sulfate salts comprise magnesium sulfate heptahydrate, iron sulfate heptahydrate and ammonium sulfate, and magnesium sulfate heptahydrate and iron sulfate heptahydrate are particularly preferable. Two or more of those inorganic salts may be used in combination.

Concentrations of the inorganic salts in liquid medium when the yellow koji molds are used are each adjusted to the extent that glucoamylase and α-amylase are selectively generated and accumulated in the koji mold culture product. To be specific, the concentration of nitrate salts is 0.1 to 2.0%, or preferably 0.2 to 1.5%, the concentration of phosphate salts is 0.05 to 1.0%, or preferably 0.1 to 0.5%, and the concentration of sulfate salts is 0.01 to 0.5%, or preferably 0.02 to 0.1%, provided that, every value is in w/vol.

Organic substances and inorganic salts except the above-mentioned inorganic salts may optionally be added to the liquid medium of the present invention as nutrient source. Those additives are not particularly limited as long as they are generally used for culturing filamentous fungi. Examples of the organic substances comprise rice bran, wheat bran, corn steep liquor, soybean cake and defatted soybean. Examples of the other inorganic salts comprise water-soluble compounds such as ammonium salts, potassium salts, calcium salts and magnesium salts. Two or more of the organic substances and/or inorganic salts may simultaneously be used. The addition amounts thereof are not particularly limited as long as growth of the filamentous fungi is promoted. The addition amount of the organic substances is preferably about 0.1 to 5% (w/vol) and the addition amount of the inorganic salts is preferably about 0.1 to 1% (w/vol).

Addition of those nutrient sources in an amount more than the upper limit is not preferable because growth of the filamentous fungus is inhibited. The addition amount less than the lower limit is also not preferable because the enzymes can not be produced in sufficient amount.

Additives such as an antibiotic or an antiseptic may optionally be added to the liquid medium in addition to those nutrient sources.

As described in the fourth aspect of the present invention, when the liquid medium which is heat treated is used in the present invention, the releasing rate of nutrients from the culture raw material into the culture system is also controlled by appropriately adjusting inorganic salt concentration in the liquid medium as heat treated.

That is, the release of nutrients from the culture raw material into the culture system is suppressed by increasing inorganic salt concentration in the liquid medium as heat treated. It is probably because physical decomposition of culture raw material is suppressed by heating the culture raw material under the presence of inorganic salts.

Examples of the inorganic salts are not particularly limited, and any of the inorganic salts which are generally used for liquid medium of filamentous fungi may be used as described above. However, nitrate salts, phosphate salts and sulfate salts are more preferable.

The inorganic salt concentration in liquid medium as heat treated may be set to 1 to 10 folds of the preferable inorganic salt concentrations in liquid medium as described above.

When the inorganic salt concentration in liquid medium as heat treated exceeds the concentration range preferable for culturing filamentous fungi, the liquid medium may be diluted after the heat treatment to appropriately adjust the inorganic salt concentration thereof, and then used for culture.

The above-mentioned heat treatment may be conducted under the conditions of a temperature of 80 to 130° C., or preferably 100 to 121° C. for 5 to 120 minutes, or preferably 10 to 30 minutes. In particular, general conditions for heat sterilization treatment of liquid medium with autoclave or the like, that is, a temperature of 110 to 121° C. for 5 to 20 minutes, are preferable because sterilization treatment of the medium is simultaneously conducted.

Next, filamentous fungi are inoculated to the liquid medium. For the filamentous fungi to be used in the present invention, there may be used widely filamentous fungi which produces enzymes affected by catabolite repression with concentrations of nutrients such as saccharide or amino acid in the culture system. Examples thereof comprise genus *Aspergillus*, genus *Trichoderma*, and one of white rot fungi, that is, *Irpex lacteus*. Specific examples of the genus *Aspergillus* comprise white koji molds typified by *Aspergillus kawachii* and the like, yellow koji molds typified by *Aspergillus oryzae*, *Aspergillus sojae* and the like, black koji molds typified by *Aspergillus awamori*, *Aspergillus niger* and the like, and *Aspergillus aculeatus*. Specific examples of the genus *Trichoderma* comprise *Trichoderma viride* and *Trichoderma reesei*, which are cellulase-producing fungi.

Those filamentous fungi may be used for the single strain culture or for the mixed culture with two or more homologous or heterogeneous strains. It is allowed to use either form of the spores or the mycelia obtained in pre-culture. However, the mycelia is preferably used because shorter times are required for the logarithmic growth phase. The amount of the filamentous fungi to be inoculated into the liquid medium is not particularly limited, but the number of the spores may be in the range of about $1 \times 10^4$ to $1 \times 10^6$ per ml of the liquid medium. In a case of the mycelia, about 0.1 to 10% of the pre-culture liquid is preferably inoculated.

The culture temperature of the filamentous fungi is preferably 25 to 45° C., or more preferably 30 to 40° C., but not particularly limited as long as the growth is not adversary affected. If the culture temperature is low, it tends to be contaminated with infectious microbes as growth of the filamentous fungi becomes slow. The culture time is preferably in the range of 24 to 120 hours. The culture apparatus may be any of those each capable of conducting liquid culture. The filamentous fungi have to be cultured aerobically. Thus, the culture should be conducted under aerobic conditions in which oxygen or air is supplied into the medium. In addition, it is preferable to stir the medium so that the raw materials, oxygen, and the filamentous fungi are uniformly distributed in the apparatus during culture. The stirring conditions and the amount of aeration may be arbitrary as long as aerobic culture environment is maintained and thus may be appropriately selected dependent on the culture apparatus, the viscosity of the medium and the like.

The second aspect of the present invention, in the above-mentioned method of producing filamentous fungus culture product, employs as culture raw material the cereals of which surface is entirely or partly covered with at least husks, and adjusts polishing ratio of the cereals to control releasing rate of nutrients from the cereals into the culture system.

In the present invention, the cereals need to have a surface entirely or partly covered with at least husks. There may be used an unpolished stuff or that having equal to or more of the polishing ratio at which it has been polished so that husks are at least remained on the surface of kernels. Crude rice, crude barley and the like can also be used. For instance, when the cereals are barley, there may be used the unpolished stuff having a polishing ratio of 100%, or provided that the polishing ratio of the unpolished stuff is defined as 100%, the stuff having a polishing ratio not less than the value determined by subtracting the husk ratio of barley (generally 7 to 8%) from the polishing ratio of the unpolished stuff, i.e., 92 to 93%.

According to the second aspect of the present invention, polishing ratio of the cereals is adjusted, and releasing rate of nutrients into the culture system is controlled so as to enhance enzymatic activity in the filamentous fungus culture product. Therefore, the optimal polishing ratio is selected dependent on species of the enzyme to be produced, kinds of the raw material cereal or the like. For instance, when glucoamylase or acid-stable α-amylase is produced by using barley as raw material, the polishing ratio is set to 90 to 100%, or more preferably 98%, whereby both enzymes is produced in high yields in a balanced manner.

The term "polishing ratio" refers to the remained percentage of cereals after the cereals are polished. For instance, the term "polishing ratio of 90%" means that 10% of the husks or the like on the surface layer portion of cereals is shaved away. In the present invention, the term "crude barley" comprises those from unpolished barley to polished barley having husks remained on the kernel's surface, that is the stuff having polishing ratios of 90% or more. The term "husk" refers to the outside part that covers the surface of a cereal particle.

Starches present in a cereal may be preliminarily gelatinized before culturing. Gelatinizing starches may be conducted according, but not particularly limited, to any one of the conventional methods comprising a steaming method, a roasting method and the like. In the step of sterilizing liquid medium as described later, when the starches are heated to the gelation temperature or higher by sterilization at high temperatures and high pressures, gelatinization of starches is simultaneously carried out by such the treatment.

The liquid medium to be used in the second aspect of the present invention is prepared by mixing water, the above-mentioned culture raw material, and other medium components. The liquid medium may be subjected to sterilization treatment if required and the procedure of such the treatment is not particularly limited. For example, it may be a high-temperature and high-pressure sterilization method carried out at a temperature of 121° C. for 15 minutes.

The third aspect of the present invention, in the above-mentioned method of producing filamentous fungus culture product, employs as culture raw material the stuff of which husks or hulls are removed, and which is not gelatinized, and releasing rate of nutrients from the culture raw material into the culture system is controlled.

In the third aspect of the present invention, it is required that the husks or hulls of the above-mentioned culture raw material are removed, and that the culture raw material is not gelatinized.

For instance, when the culture raw material is barley, the stuff having a polishing ratio not less than the value determined by subtracting the husk ratio of barley (generally 7 to 8%) from the polishing ratio of the unpolished stuff (100%), i.e., about 92 to 93%. Pearled barley (having a polishing ratio of 65%) may also be used.

The above-mentioned culture raw material is not subjected to the treatment, such as heating, by which the starch therein is gelatinized. However, the above-mentioned culture raw material may be subjected to treatments such as threshing, polishing, peeling, washing, chopping, crushing, and freezing as required.

In the third aspect of the present invention, the blending ratio of the above-mentioned culture raw material in liquid medium is set to the extent that glucoamylase and acid-stable α-amylase are selectively generated and accumulated in the filamentous fungus culture product. To be specific, the culture raw material may be added in an amount of 1 to 10% (w/vol), preferably 2 to 6% (w/vol) with respect to the liquid medium. However, the blending ratio may appropriately be selected because the optimal blending ratio varies dependent on kinds of the filamentous strain to be used, the culture raw materials and the like.

In the case where aerobic filamentous fungi are used, if the amount of the culture raw material to be used exceeds the upper limit, viscosity of the culture liquid increases and supply of oxygen or air required for aerobically culturing filamentous fungi becomes insufficient. That decreases oxygen content in the culture product, restricts culture progress, and is not preferred. On the other hand, when the amount of the raw material to be used is less than the lower limit, glucoamylase and acid-stable α-amylase can not be produced in high yields.

The liquid medium used in the third aspect of the present invention is prepared by mixing water, the above-mentioned culture raw material and other medium components. In this case, if required, medium components except the culture raw material is mixed with water, the mixture is sterilized in advance, and then starch-containing raw material which is not gelatinized may additionally be added thereto. Alternatively, there may be adopted a method that a part of culture raw material and other medium components are mixed with water, the mixture is sterilized in advance, and then the balance of the culture raw material which is not gelatinized is added thereto.

The sterilization method is not particularly limited. For example, it may be a high-temperature and high-pressure sterilization method carried out at a temperature of 121° C. for 15 minutes.

Filamentous fungi are cultured by the above-mentioned culture method to obtain a filamentous fungus culture product in which the intended enzymes are efficiently generated and accumulated. The filamentous fungus culture product in the present invention comprises, in addition to the culture product itself, a culture liquid obtained by subjecting the culture product to centrifugal separation or the like, a concentrate thereof, a purified product thereof, or a dry product thereof and the like.

As described above, according to the above-mentioned culture method, there may be highly produced a group of enzymes, the productivity of which is affected by the catabolite repression with concentrations of saccharide such as glucose or decomposed protein such as amino acid in the culture system.

Thus, the method of producing enzymes according to the eleventh aspect of the present invention is the same as the above-mentioned method of producing filamentous fungus culture product.

The filamentous fungus culture product obtained by the present invention is used not only for producing fermented foods and drinks, but also for producing saccharides, amino acids, derivatives thereof, an enzyme preparation and a pharmaceutical digestive agent. The koji mold culture product may be used instead of the solid koji, for instance, in the case of producing Sake, at the stage of preparing yeast mash or sake mash; in the case of producing shochu, at the stage of mashing shochu mash; in the case of producing soy sauce, at the stage of piling; in the case of producing miso, at the stage of mashing; in the case of producing brewed vinegar, at the stage of mashing; in the case of producing sweet sake, at the stage of mashing; and in the case of producing amazake, at the stage of mashing. The fermentation raw material (additional raw material) to be used for producing those fermented foods and drinks may be gelatinized or may not be gelatinized.

A part of the resultant filamentous fungus culture product may be used as starter for subsequent production of filamentous fungus culture product. By producing filamentous fungus culture products consecutively in this manner, stable production is achieved and production efficiency is improved at the same time.

As a method of producing enzyme preparation from the filamentous fungus culture product of the present invention, the culture product itself, filtrate thereof, supernatant by centrifugal separation and the like may be employed as a liquid enzyme preparation, or it may be dried or immobilized to support by a conventional method to preparation. Appropriate excipient or the like may be added thereto at this time.

When fermented foods and drinks such as alcohol beverages are produced using the above-mentioned filamentous fungus culture product, all the step may be carried out in liquid phase. For instance, when shochu is produced, corn, wheat, rice, potato, sugar cane and the like are used as raw material and then heated at about 80° C. to liquefy by dissolving with a heat-resistant enzyme preparation, the above-mentioned koji mold culture product and yeast are added thereto to allow the mash to alcohol ferment, and then it is distillated under normal pressure or reduced pressure and the like.

EXAMPLES

Hereinafter, the present invention will be described in more detail by way of examples. However, the present invention is not limited to these examples.

Experimental Example 1

Measurement of Glucose Liberation Rate from Barley Having Various Polishing Ratios Barley (Stirling, made in Australia) having various polishing ratios of from 65% to 98% was allowed to react with enzymes derived from koji mold culture product, and glucose liberation rates from the barley were measured.

To be specific, 2 g of each of 65%-polished barley, 83%-polished barley, 92%-polished barley, 95%-polished barley, 98%-polished barley and a 98%-polished barley crushed product were weighed out, and each of the weighed materials and 50 ml of water were put in a 200-ml conical flask. This was sterilized with autoclave at 121° C. for 15 minutes to prepare "barley substrate solution".

Subsequently, a koji mold culture product produced by using barley (Stirling, made in Australia) as culture raw material was subjected to solid-liquid separation by filtration with filtering paper to obtain "a koji mold culture supernatant".

The method of producing the koji mold culture product used in this experiment were as described below.

1. Method of Pre-Culture 8 g of 65%-polished barley and 100 ml of water were put in a 500-ml baffled conical flask, and was sterilized at 121° C. for 15 minutes with autoclave to obtain a pre-culture medium. After cooling, a white koji mold (Aspergillus kawachii NBRC4308) was inoculated at $1\times10^6$/ml into the pre-culture medium and cultured with shaking at 37° C. and 100 rpm for 24 hours to obtain a pre-culture liquid.

2. Method of Main Culture

98%-polished barley was added to water supplemented with 0.2% (w/vol) potassium nitrate and 0.3% (w/vol) potassium dihydrogen phosphate so that the amount of 98%-polished barley was 2.0% (w/vol) to prepare liquid medium. 3,000 ml of the prepared liquid medium was put in a 5,000-ml jar fermentor (manufactured by B. E. Marubishi Co., Ltd.), and was sterilized with autoclave (at 121° C. for 15 minutes), followed by inoculating with 30 ml of the pre-culture liquid of the white koji mold (Aspergillus kawachii NBRC4308) pre-cultured in advance in the liquid medium by the above-mentioned method. After that, culture was conducted for 42 hours at a temperature of 37° C. and a stirring rate of 300 rpm and with an aeration volume of 0.5 vvm, and the resultant was filtrated with filtering paper (Toyo filter paper No. 2) to obtain "a koji mold culture supernatant".

3. Method of Measurement 50 ml of the thus-prepared barley substrate solution and 50 ml of the thus-prepared koji mold culture supernatant were separately kept at 37° C. for 5 minutes, and were then mixed to start reaction. Glucose concentrations in reaction liquids sampled after 1 hour, 2 hours, 3 hours, and 4 hours after the initiation of the reaction were measured with Glucose C-II Test Wako (manufactured by Wako Pure Chemical Industries Co., Ltd.).

4. Results

Temporal changes of the glucose concentrations in the reaction liquids were as shown in FIG. 1. It was confirmed that amounts of liberated glucose differ dependent on the polishing degrees of the barley used for the barley substrate solutions. In general, barley has husks percentage of about 10%, and the 65%-polished barley and the 83%-polished barley each of which were used in this experiment have no husks on the surface thereof. In contrast, the 92%-polished barley, the 95%-polished barley and the 98%-polished barley have husks remained on the surfaces thereof.

As shown in FIG. 1, experimental plots in which the 65%- and 83%-polished barley each of which had no husk on the surface thereof and the 98%-polished barley crushed product were used, respectively, showed high glucose concentrations. In contrast, in experimental plots in which the 92%-, 95%-, and 98%-polished barley were used, respectively, it was confirmed that the glucose concentration is low as the polishing ratio is low. For this reason, it was revealed that the amount of liberated glucose was controlled by the presence of husks.

Figure 2:
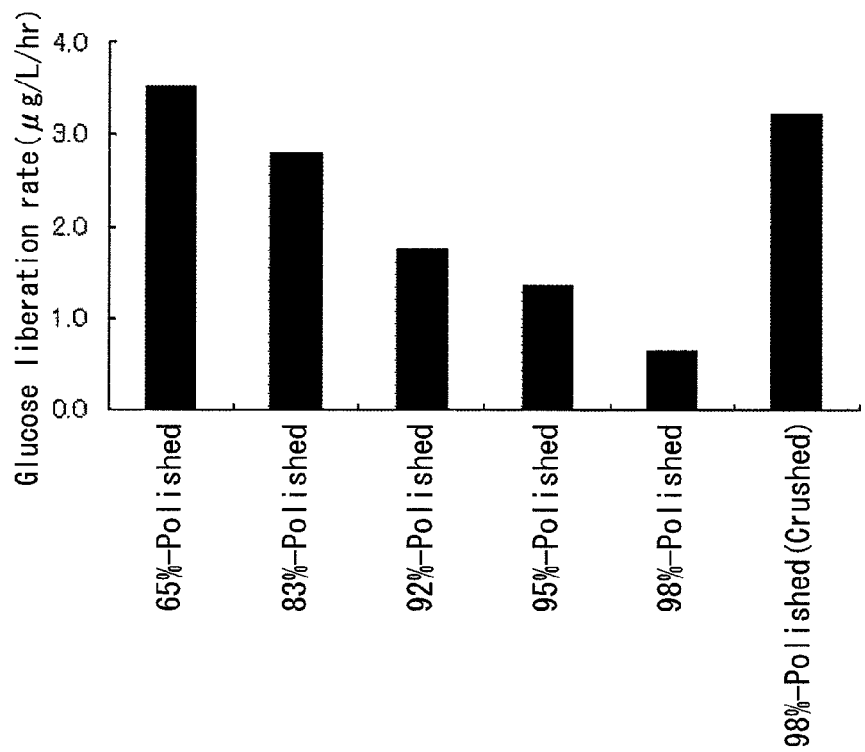
FIG. 2 shows glucose liberation rates for the first 1 hour of the reactions in which barley substrate solutions containing barley having various polishing ratios are allowed to react with koji molds culture supernatant, respectively.

FIG. 2 shows calculated values of glucose liberation rates for the first 1 hour of the reaction in this experiment. From FIG. 2, it was confirmed that the glucose liberation rate was controlled low as the polishing ratio is low.

On the other hand, in the experimental plot in which the 98%-polished barley crushed product was used, the glucose liberation rate increased to a level equivalent to that of the 65%-polished barley. Thus, the husks physically covering starch components of barley is suggested to be a main factor for that the glucose liberation rate is adjusted.

Example 1

Production of White Koji Culture Product Using Barley Having Various Polishing Ratios White koji mold culture products were produced by using various degrees of polished barley (Stirling, made in Australia) by the method as described below, and enzymatic activities therein were measured.

1. Method of Pre-Culture 8 g of 65%-polished barley and 100 ml of water were put in a 500-ml baffled conical flask, and was sterilized at 121° C. for 15 minutes with autoclave to obtain a pre-culture medium. After cooling, a white koji mold (Aspergillus kawachii NBRC4308) was inoculated at $1\times10^6$/ml into the pre-culture medium and cultured with shaking at 37° C. and 100 rpm for 24 hours to obtain a pre-culture liquid.

2. Method of Main Culture 2 g of any one of 65%-polished barley, 83%-polished barley, 92%-polished barley, 95%-polished barley and 98%-polished barley, 0.2 g of potassium nitrate, 0.3 g of potassium dihydrogen phosphate and 100 ml of water were put in a 500-ml baffled conical flask, and was sterilized at 121° C. for 15 minutes with autoclave to prepare a main culture medium. After cooling, the main culture medium was inoculated with 1 ml of the pre-culture liquid, and cultured with shaking at 37° C. and 100 rpm for 48 hours.

3. Method of Measurement

After the culture was completed, activities of glucoamylase (GA), α-amylase (AA) and acid-stable α-amylase (ASAA), that are amylolytic enzymes, were measured.

The glucoamylase (GA) activity was measured by using a saccharification power fractional quantification kit (manufactured by Kikkoman Corporation), and the α-amylase (AA) activity was measured by using an α-amylase measurement kit (manufactured by Kikkoman Corporation). For measuring the acid-stable α-amylase (ASAA) activity, the method described in Sudo S. et al: J. Ferment. Bioeng., 76, 105-110 (1993), Sudo S. et al: J. Ferment. Bioeng., 77, 483-489 (1994), and Shigetoshi Sudo et al: Journal of the Brewing Society of Japan, 89, 768-774 (1994) was slightly modified. That is, acid-unstable α-amylase activity was inactivated by treating the culture product with acid, and then acid-stable α-amylase activity was measured with an α-amylase measurement kit (manufactured by Kikkoman Corporation) To be more specific, 9 ml of 100 mM acetic acid buffer liquid (pH 3) was added to 1 ml of culture liquid, and acid treatment was conducted at 37° C. for 1 hour, and measured with the α-amylase measurement kit (manufactured by Kikkoman Corporation).

The activities of cellulase (CEL) and β-glucosidase (BGL) that are cellulolytic enzymes were then measured. The cellulase (CEL) activity was measured by the method that amount of the reduced saccharide which is generated from hydrolysis of carboxymethylcellulose (CMC) as substrate was quantitated by the dinitrosalicylic acid (DNS) method. To be more specific, 1 ml of the culture liquid was added to 1 ml of 1% CMC substrate solution (a solution obtained by dissolving low Viscosity™ produced by Sigma-Aldrich in a 100 mM acetic acid buffer liquid (pH 5)), and enzymatic reaction was allowed to proceed at 40° C. exactly for 10 minutes. After that, 4 ml of the DNS reagent containing 0.75% of dinitrosalicylic acid, 1.2% of sodium hydroxide, 22.5% of potassium sodium tartrate tetrahydrate and 0.3% of lactose monohydrate, was added to the mixture, and well mixed to terminate the reaction. In order to quantitate the amount of reduced saccharide in the liquid after terminating the reaction, the liquid after terminating the reaction was heated in boiling water bath exactly for 15 minutes. Subsequently, the liquid was cooled to room temperature, absorbance at 540 nm was determined to quantitate amount of the reduced saccharide corresponding to that of glucose. One unit of cellulase (CEL) activity represents the amount of enzyme required for producing reduced saccharide which corresponds to 1 μmol of glucose per minute.

The β-glucosidase activity was measured by the method as described below. Enzymatic reaction was conducted at 37° C. for exactly 10 minutes in 50 mM acetic acid buffer liquid (pH 5) using 1 mM p-nitrophenyl-β-D-glucopyranoside (PNPG) as substrate. After the reaction was terminated, amount of generated p-nitrophenol was quantitated by absorbance at 410 nm to calculate the enzymatic activity. The reaction was terminated by adding thereto 200 mM sodium carbonate solution in double amount of the reaction liquid. One unit of activity represents the activity by which 1 μmol of glucose is liberated per minute.

Figure 3:
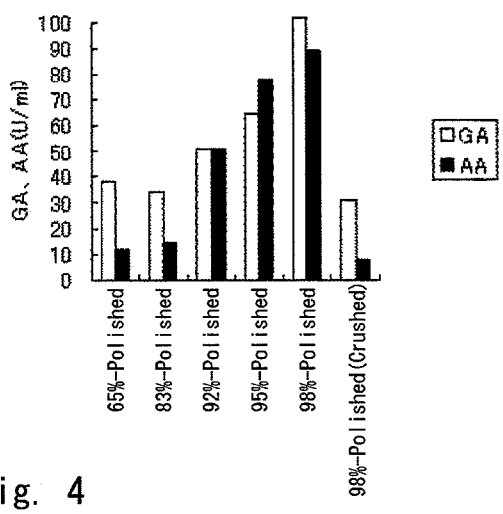
FIG. 3 each show enzymatic activities in white koji mold culture products obtained by using barley having various polishing ratios as culture raw material.
Figure 3:
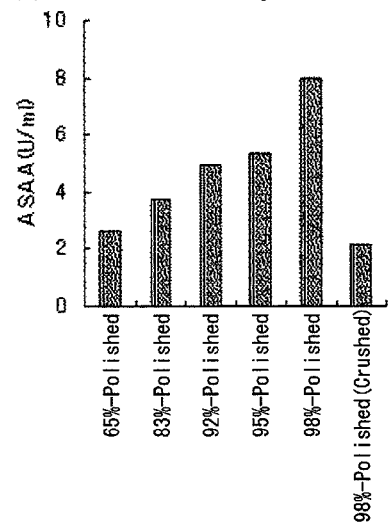
Figure 4:
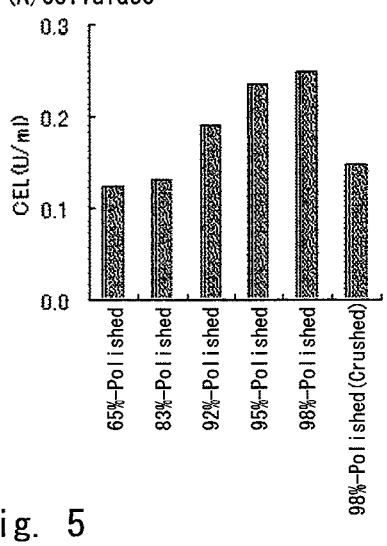
FIG. 4 each show enzymatic activities in white koji mold culture products obtained by using barley having various polishing ratios as culture raw material.
Figure 4:
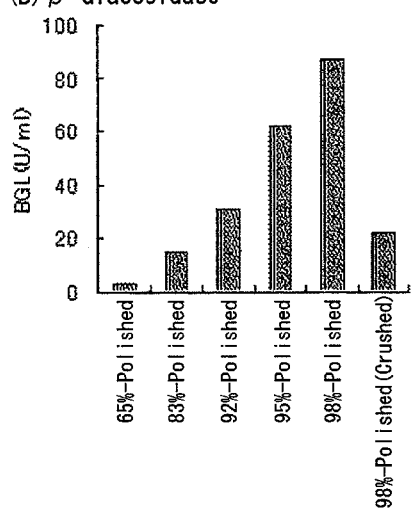

FIGS. 3 and 4 show the measurement results.

4. Results

As shown in FIG. 3, productivity of the amylolytic enzymes was increased as the polishing ratio was decreased. Even with the 98%-polished barley having low polishing ratio, the enzymatic productivity therein was significantly decreased when the barley was crushed. Further, as shown in FIG. 4, there was observed a tendency that productivity of the cellulolytic enzymes was increased as the polishing ratio was decreased. In this manner, there was observed the tendency of the enzymatic productivity in the white koji mold culture product to have inverse correlation to the glucose liberation rate as shown in Experimental Example 1, and it was revealed that the enzymatic productivity in white koji mold culture product was controlled by changing a polishing ratio of barley.

Example 2

Production of Black Koji Mold Culture Product Using Barley Having Various Polishing Ratios Black koji mold culture products were produced by using various degrees of polished barley (Stirling, made in Australia) by the method as described below, and enzymatic activities therein were measured.

1. Method of Pre-Culture 8 g of 65%-polished barley and 100 ml of water were put in a 500-ml baffled conical flask, and was sterilized at 121° C. for 15 minutes with autoclave to obtain a pre-culture medium. After cooling, a black koji mold (*Aspergillus awamori* NBRC4388) was inoculated at $1 \times 10^6$/ml into the pre-culture medium and cultured with shaking at 37° C. and 100 rpm for 24 hours to obtain a pre-culture liquid.

2. Method of Main Culture 2 g of any one of 65%-polished barley, 83%-polished barley, 92%-polished barley, 95%-polished barley and 98%-polished barley, 0.2 g of potassium nitrate, 0.3 g of potassium dihydrogen phosphate and 100 ml of water were put in a 500-ml baffled conical flask, and was sterilized at 121° C. for 15 minutes with autoclave to prepare a main culture medium. After cooling, the main culture medium was inoculated with 1 ml of the pre-culture liquid, and cultured with shaking at 37° C. and 100 rpm for 48 hours.

3. Method of Measurement

After the culture was completed, activities of glucoamylase (GA), α-amylase (AA) and acid-stable α-amylase (ASAA), that are amylolytic enzymes, were measured.

The glucoamylase (GA) activity was measured by using a saccharification power fractional quantification kit (manufactured by Kikkoman Corporation), and the α-amylase (AA) activity was measured by using an α-amylase measurement kit (manufactured by Kikkoman Corporation). For measuring the acid-stable α-amylase (ASAA) activity, the method described in Sudo S. et al: J. Ferment. Bioeng., 76, 105-110 (1993), Sudo S. et al: J. Ferment. Bioeng., 77, 483-489 (1994), and Shigetoshi Sudo et al: Journal of the Brewing Society of Japan, 89, 768-774 (1994) was slightly modified. That is, acid-unstable α-amylase activity was inactivated by treating the culture product with acid, and then acid-stable α-amylase activity was measured with an α-amylase measurement kit (manufactured by Kikkoman Corporation). To be more specific, 9 ml of 100 mM acetic acid buffer liquid (pH 3) was added to 1 ml of culture liquid, and acid treatment was conducted at 37° C. for 1 hour, and measured with the α-amylase measurement kit (manufactured by Kikkoman Corporation).

Figure 5:
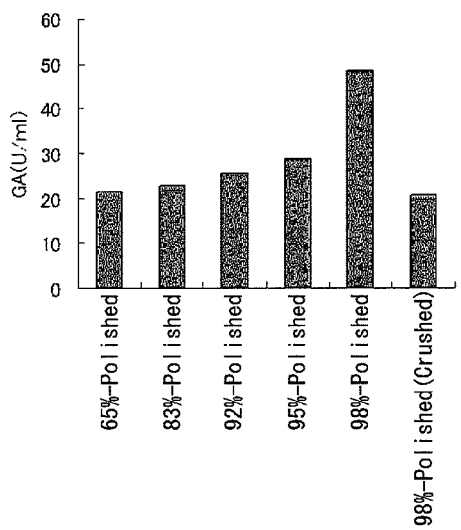
FIG. 5 shows glucoamylase (GA) activities in black koji mold culture products using barley having various polishing ratios as culture raw material.
Figure 6:
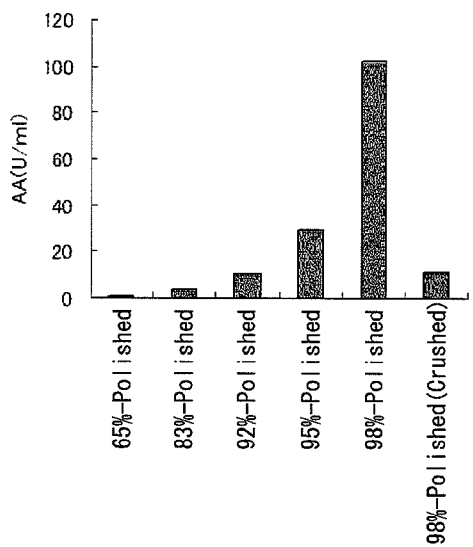
FIG. 6 shows α-amylase (AA) activities in black koji mold culture products using barley having various polishing ratios as culture raw material.
Figure 7:
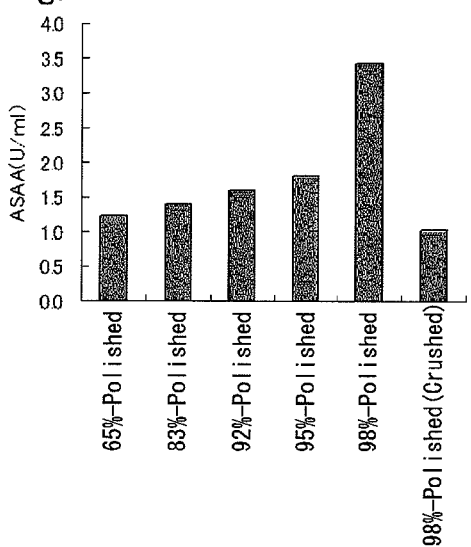
FIG. 7 shows acid-stable α-amylase (ASAA) activities in black koji mold culture products using barley having various polishing ratios as culture raw material.

FIGS. 5 to 7 show the measurement results.

4. Results

As shown in FIGS. 5 to 7, productivity of the amylolytic enzymes was increased as the polishing ratio was decreased. Even with the 98%-polished barley having low polishing ratio, the enzymatic productivity therein was significantly decreased when the barley was crushed. In this manner, there was observed the tendency of the enzymatic productivity in the black koji mold culture product to have inverse correlation to the glucose liberation rate as shown in Experimental Example 1, and it was reveled that the enzymatic productivity in a black koji mold culture product was controlled by changing polishing ratio of barley.

Example 3

Production of Yellow Koji Mold Culture Product Using Barley Having Various Polishing Ratios Yellow koji mold culture products were produced by using various degrees of polished barley (Stirling, made in Australia) by the method as described below, and enzymatic activities therein were measured.

1. Method of Culture 100 ml of medium containing 2 g of any one of 65%-polished barley, 83%-polished barley, 92%-polished barley, 95%-polished barley and 98%-polished barley, 1.2% (w/vol)

of sodium nitrate, 0.8% (w/vol) of potassium chloride, 0.4% (w/vol) of potassium dihydrogen phosphate, 0.2% (w/vol) of magnesium sulfate heptahydrate, 0.08% (w/vol) of iron sulfate heptahydrate and water was put in a 500-ml baffled conical flask, and sterilized at 121° C. for 15 minutes with autoclave to prepare a medium. After cooling, a yellow koji mold (*Aspergillus oryzae* RIB40) was inoculated at $1 \times 10^6$/ml into the pre-culture medium and cultured with shaking at 30° C. and 100 rpm for 72 hours.

2. Method of Measurement

After the culture was completed, activities of glucoamylase (GA) and α-amylase (AA), that are amylolytic enzymes, were measured.

The glucoamylase (GA) activity was measured by using a saccharification power fractional quantification kit (manufactured by Kikkoman Corporation), and the α-amylase (AA) activity was measured by using an α-amylase measurement kit (manufactured by Kikkoman Corporation).

Figure 8:
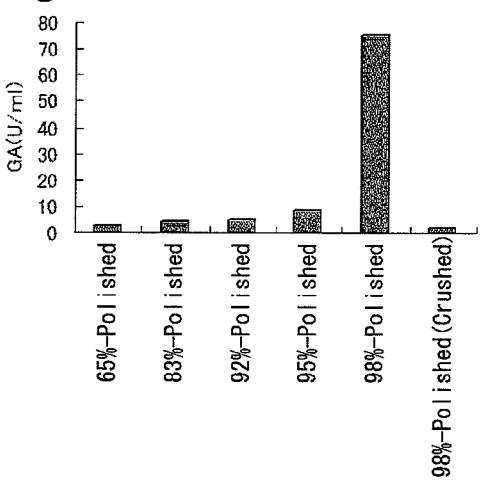
FIG. 8 shows glucoamylase (GA) activities in yellow koji mold culture products using barley having various polishing ratios as culture raw material.
Figure 9:
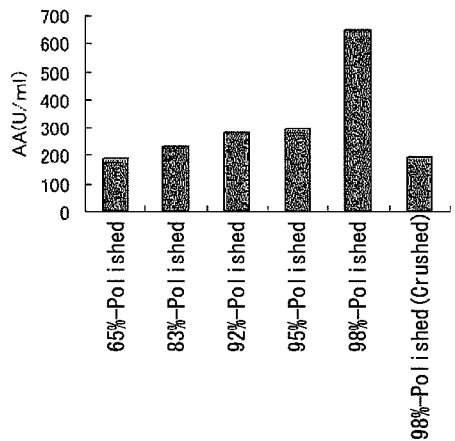
FIG. 9 shows α-amylase (AA) activities in yellow koji mold culture products using barley having various polishing ratios as culture raw material.

FIGS. 8 and 9 show the measurement results.

3. Results

As shown in FIGS. 8 and 9, productivity of the amylolytic enzymes was increased as the polishing ratio was decreased. In particular, activity of glucoamylase significantly increased when the 98%-polished barley was used. Even with the 98%-polished barley having low polishing ratio, the enzymatic productivity therein significantly decreased when crushed barley thereof was used. As described above, it was revealed that the enzymatic productivity in yellow koji mold culture product is greatly influenced by glucose liberation rate as shown in Experimental Example 1, and that enzymatic productivity in yellow koji mold culture product is controlled by changing polishing ratio of barley.

Example 4

Production of Filamentous Fungus (*Trichoderma viride*) Culture Product by Using Barley Having Various Polishing Ratios Culture products of a filamentous fungus (*Trichoderma viride*) capable of producing cellulolytic enzymes were produced by using various degrees of polished barley (Stirling, made in Australia) by the method as described below, and enzymatic activities therein were measured.

1. Method of Pre-Culture 100 ml of medium containing 2% of glucose, 0.5% of an yeast extract, 0.1% of potassium nitrate, 0.1% of monopotassium hydrogen phosphate, 0.07% of ammonium sulfate, 0.03% of magnesium sulfate heptahydrate, 0.02% of calcium chloride (every % is in w/vol) and water was put in a 500-ml baffled conical flask, and was sterilized at 121° C. for 15 minutes with autoclave to prepare a pre-culture medium. After cooling, *Trichoderma viride* (*Torichoderma viride* NBRC31137) was inoculated at $1 \times 10^6$/ml into the pre-culture medium and cultured with shaking at 30° C. and 100 rpm for 24 hours to obtain a pre-culture liquid.

2. Method of Main Culture 100 ml of medium containing 2% of polished barley, 0.08% of triptone, 0.25% of ammonium sulfate, 0.1% of ammonium phosphate, 0.03% of calcium chloride, 0.03% of magnesium sulfate heptahydrate, 0.12% of potassium nitrate (every % is in w/vol) and water was put in a 500-ml baffled conical flask, and was sterilized at 121° C. for 15 minutes with autoclave to obtain a main culture medium.

65%-polished barley, 83%-polished barley, 92%-polished barley, 95%-polished barley, 98%-polished barley or a 98%-polished barley crushed product was used as the above-mentioned polished barley.

After cooling, the main culture medium was inoculated with 10 ml of the pre-culture liquid, and cultured with shaking at 30° C. and 100 rpm for 90 hours.

3. Method of Measurement

After the culture was completed, activity of cellulase (CEL) that is cellulolytic enzyme was measured. The cellulase (CEL) activity was measured by the method that amount of the reduced saccharide which is generated from hydrolysis of carboxymethylcellulose (CMC) as substrate was quantitated by the dinitrosalicylic acid (DNS) method. To be more specific, 1 ml of the culture liquid was added to 1 ml of 1% CMC substrate solution (a solution obtained by dissolving low Viscosity™ produced by Sigma-Aldrich in a 100 mM acetic acid buffer liquid (pH 5)), and enzymatic reaction was allowed to proceed at 40° C. exactly for 10 minutes. After that, 4 ml of the DNS reagent containing 0.75% of dinitrosalicylic acid, 1.2% of sodium hydroxide, 22.5% of potassium sodium tartrate tetrahydrate and 0.3% of lactose monohydrate, was added to the mixture, and well mixed to terminate the reaction. In order to quantitate the amount of reduced saccharide in the liquid after terminating the reaction, the liquid after terminating the reaction was heated in boiling water bath exactly for 15 minutes. Subsequently, the liquid was cooled to room temperature, absorbance at 540 nm was determined to quantitate amount of the reduced saccharide corresponding to that of glucose. One unit of cellulase (CEL) activity represents the amount of enzyme required for producing reduced saccharide which corresponds to 1 μmol of glucose per minute.

4. Results

Figure 10:
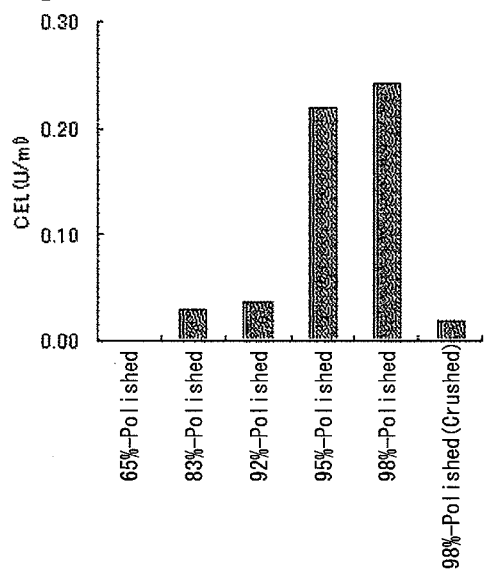
FIG. 10 shows cellulase (CEL) activities in *Trichoderma viride* culture products using barley having various polishing ratios as culture raw material.

FIG. 10 shows the measurement results. It was confirmed that cellulose productivity differed dependent on the polishing ratio also in *Trichoderma viride* that is a filamentous fungus except koji molds. The 98%-polished barley provided the highest enzymatic productivity, whereas the crushed product thereof significantly decreased in enzymatic activity. Thus, it was suggested that nutrient release suppressing effect of barley husks contributes to the high production of cellulase.

Example 5

Production of Filamentous Fungus (*Trichoderma reesei*) Culture Product by Using Barley Having Various Polishing Ratios Culture products of a filamentous fungus (*Trichoderma reesei*) capable of producing cellulolytic enzymes were produced by using various degrees of polished barley (Stirling, made in Australia) by the method as described below, and enzymatic activities therein were measured.

1. Method of Culture (1) Method of Pre-Culture 100 ml of medium containing 2% of glucose, 0.5% of an yeast extract, 0.1% of potassium nitrate, 0.1% of monopotassium hydrogen phosphate, 0.07% of ammonium sulfate, 0.03% of magnesium sulfate heptahydrate, 0.02% of calcium chloride (every % is in w/vol) and water was put in a 500-ml baffled conical flask, and was sterilized at 121° C. for 15 minutes with autoclave to prepare a pre-culture medium. After cooling, *Trichoderma reesei* (*Torichoderma reesei* NBRC31326) was inoculated at $1 \times 10^6$/ml into the pre-culture medium and cultured with shaking at 30° C. and 100 rpm for 72 hours to obtain a pre-culture liquid.

(2) Method of Main Culture 100 ml of medium containing 2% of polished barley, 0.08% of triptone, 0.25% of ammonium sulfate, 0.1% of ammonium phosphate, 0.03% of calcium chloride, 0.03% of magnesium sulfate heptahydrate, 0.12% of potassium nitrate (every % is in w/vol) and water was put in a 500-ml baffled conical flask, and was sterilized at 121° C. for 15 minutes with autoclave to obtain a main culture medium.

65%-polished barley, 83%-polished barley, 95%-polished barley, 98%-polished barley or a 98%-polished barley crushed product was used as the above-mentioned polished barley.

After cooling, the main culture medium was inoculated with 10 ml of the pre-culture liquid, and cultured with shaking at 30° C. and 100 rpm for 96 hours.

2. Method of Measuring Enzymatic Activity

After the culture was completed, the culture liquid was centrifuged to collect a supernatant, and activities of plant fiber degradation enzymes in the supernatant were measured.

(1) Method of Measuring Cellulase Activity

The cellulase (CEL) activity was measured by the method that amount of the reduced saccharide which is generated from hydrolysis of carboxymethylcellulose (CMC) as substrate was quantitated by the dinitrosalicylic acid (DNS) method. To be more specific, 1 ml of the culture liquid was added to 1 ml of 1% CMC substrate solution (a solution obtained by dissolving low Viscosity™ produced by Sigma-Aldrich in a 100 mM acetic acid buffer liquid (pH 5)), and enzymatic reaction was allowed to proceed at 40° C. exactly for 10 minutes. After that, 4 ml of the DNS reagent containing 0.75% of dinitrosalicylic acid, 1.2% of sodium hydroxide, 22.5% of potassium sodium tartrate tetrahydrate and 0.3% of lactose monohydrate, was added to the mixture, and well mixed to terminate the reaction. In order to quantitate the amount of reduced saccharide in the liquid after terminating the reaction, the liquid after terminating the reaction was heated in boiling water bath exactly for 15 minutes. Subsequently, the liquid was cooled to room temperature, absorbance at 540 nm was determined to quantitate amount of the reduced saccharide corresponding to that of glucose. One unit of cellulase (CEL) activity represents the amount of enzyme required for producing reduced saccharide which corresponds to 1 µmol of glucose per minute.

(2) Method of Measuring Xylanase Activity

Next, the xylanase (XYL) activity was measured by allowing the reduced saccharide which is generated by enzymatic hydrolysis of xylan derived from oat spelts as substrate to react with DNS, and quantitating the increase of absorbance at 540 nm. To be more specific, 0.1 ml of the culture liquid was added to 1.9 ml of 1% xylan substrate solution (xylan, from oat spelts produced by Sigma-Aldrich dissolved in a 200 mM acetic acid buffer liquid (pH 4.5)), and enzymatic reaction was allowed to proceed at 40° C. exactly for 10 minutes. After that, 4 ml of the DNS reagent containing 0.75% of dinitrosalicylic acid, 1.2% of sodium hydroxide, 22.5% of potassium sodium tartrate tetrahydrate and 0.3% of lactose monohydrate, was added to the mixture, and well mixed to terminate the reaction. In order to quantitate the amount of reduced saccharide in the liquid after terminating the reaction, the liquid after terminating the reaction was heated in boiling water bath exactly for 15 minutes. Subsequently, the liquid was cooled to room temperature, absorbance at 540 nm was determined to quantitate amount of the reduced saccharide corresponding to that of xylose. One unit of xylanase activity represents the amount of enzyme required for producing reduced saccharide which corresponds to 1 µmol of xylose per minute under the reaction condition of 40° C. and 10 minutes.

(3) Method of Measuring β-Glucosidase Activity

The β-glucosidase (BGL) activity was measured by the method as described below. Enzymatic reaction was conducted at 37° C. for exactly 10 minutes in 50 mM acetic acid buffer liquid (pH 5) using 1 mM p-nitrophenyl-β-D-glucopyranoside (PNPG) as substrate. After the reaction was terminated, amount of generated p-nitrophenol was quantitated by absorbance at 410 nm to calculate the enzymatic activity. The reaction was terminated by adding 200 mM sodium carbonate solution in twice amount of the reaction liquid. One unit of activity represents the activity by which 1 µmol of glucose is liberated per minute.

3. Results

Figure 11:
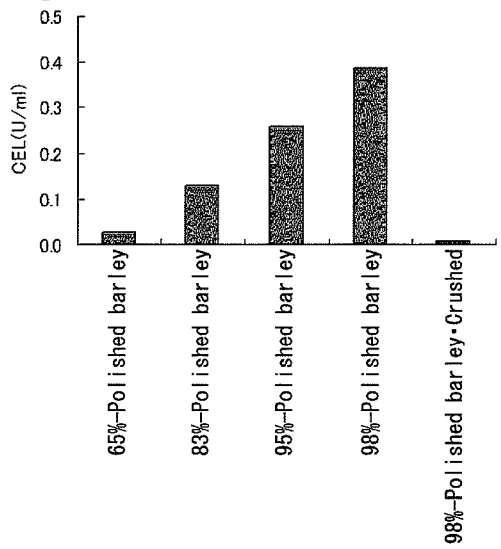
FIG. 11 shows cellulase (CEL) activities in *Trichoderma reesei* culture products using barley having various polishing ratios as culture raw material.
Figure 12:
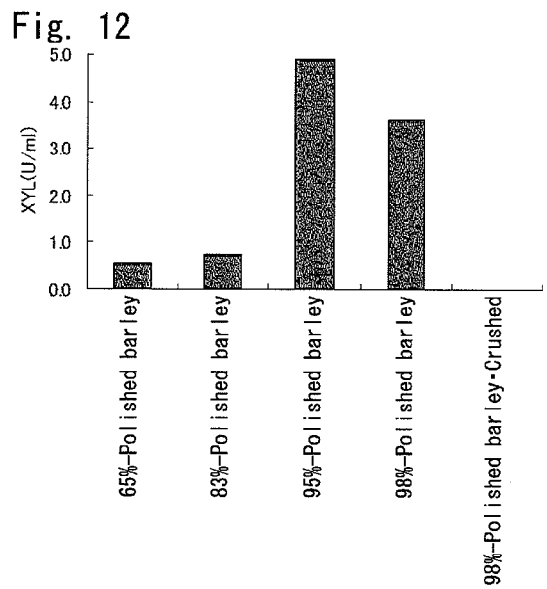
FIG. 12 shows xylanase (XYL) activities in *Trichoderma reesei* culture products using barley having various polishing ratios as culture raw material.
Figure 13:
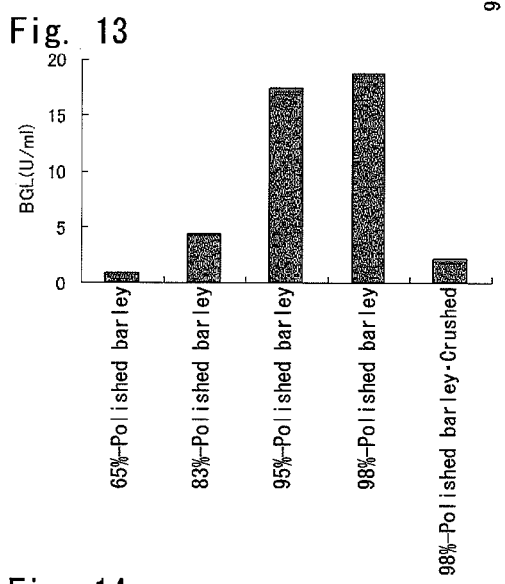
FIG. 13 shows β-glucosidase (BGL) activities in *Trichoderma reesei* culture products using barley having various polishing ratios as culture raw material.

FIGS. 11 to 13 show the measurement results. It was confirmed that productivity of plant fiber degradation enzyme was differed by the polishing ratio also in *Trichoderma reesei* that is a filamentous fungus except the koji molds. High enzymatic productivity was obtained when the 95%- or 98%-polished barley was used. However, the enzymatic activity significantly decreased when the 98%-polished barley crushed product was used. Thus, it was suggested that the nutrient release suppressing effect of barley husks on the release of nutrients contributes to the high production of the plant fiber degradation enzymes.

Example 6

Production of Filamentous Fungus (*Aspergillus aculeatus*) Culture Product Using Barley Having Various Polishing Ratios Culture products of a filamentous fungus (*Aspergillus aculeatus*) capable of producing cellulolytic enzymes were produced by using various degrees of polished barley (Stirling, made in Australia) by the method as described below, and enzymatic activities therein were measured.

1. Method of Culture (1) Method of Pre-Culture 100 ml of medium containing 2% of glucose, 0.5% of an yeast extract, 0.1% of potassium nitrate, 0.1% of monopotassium hydrogen phosphate, 0.07% of ammonium sulfate, 0.03% of magnesium sulfate heptahydrate, 0.02% of calcium chloride (every % is in w/vol) and water was put in a 500-ml baffled conical flask, and was sterilized at 121° C. for 15 minutes with autoclave to prepare a pre-culture medium. After cooling, *Aspergillus aculeatus* (*Aspergillus aculeatus* NBRC3530) was inoculated at 1×10⁶/ml into the pre-culture medium and cultured with shaking at 30° C. and 100 rpm for 72 hours to obtain a pre-culture liquid.

(2) Method of Main Culture 100 ml of medium containing 2% of polished barley, 0.08% of triptone, 0.25% of ammonium sulfate, 0.1% of ammonium phosphate, 0.03% of calcium chloride, 0.03% of magnesium sulfate heptahydrate, 0.12% of potassium nitrate (every % is in w/vol) and water was put in a 500-ml baffled conical flask, and was sterilized at 121° C. for 15 minutes with autoclave to obtain a main culture medium.

65%-polished barley, 83%-polished barley, 95%-polished barley, 98%-polished barley or a 98%-polished barley crushed product was used as the above-mentioned polished barley.

After cooling, the main culture medium was inoculated with 10 ml of the pre-culture liquid, and cultured with shaking at 30° C. and 100 rpm for 96 hours.

2. Method of Measuring Enzymatic Activity

After the culture was completed, the culture liquid was centrifuged to collect a supernatant, and activities of plant fiber degradation enzymes in the supernatant were measured.

(1) Method of Measuring Cellulase Activity

The cellulase (CEL) activity was measured by the method that amount of the reduced saccharide which is generated from hydrolysis of carboxymethylcellulose (CMC) as substrate was quantitated by the dinitrosalicylic acid (DNS) method. To be more specific, 1 ml of the culture liquid was added to 1 ml of 1% CMC substrate solution (a solution obtained by dissolving low Viscosity™ produced by Sigma-Aldrich in a 100 mM acetic acid buffer liquid (pH 5)), and enzymatic reaction was allowed to proceed at 40° C. exactly for 10 minutes. After that, 4 ml of the DNS reagent containing 0.75% of dinitrosalicylic acid, 1.2% of sodium hydroxide, 22.5% of potassium sodium tartrate tetrahydrate and 0.3% of lactose monohydrate, was added to the mixture, and well mixed to terminate the reaction. In order to quantitate the amount of reduced saccharide in the liquid after terminating the reaction, the liquid after terminating the reaction was heated in boiling water bath exactly for 15 minutes. Subsequently, the liquid was cooled to room temperature, absorbance at 540 nm was determined to quantitate amount of the reduced saccharide corresponding to that of glucose. One unit of cellulase (CEL) activity represents the amount of enzyme required for producing reduced saccharide which corresponds to 1 µmol of glucose per minute.

(2) Method of Measuring β-Glucosidase Activity

The β-glucosidase (BGL) activity was measured by the method as described below. Enzymatic reaction was conducted at 37° C. for exactly 10 minutes in 50 mM acetic acid buffer liquid (pH 5) using 1 mM p-nitrophenyl-β-D-glucopyranoside (PNPG) as substrate. After the reaction was terminated, amount of generated p-nitrophenol was quantitated by absorbance at 410 nm to calculate the enzymatic activity. The reaction was terminated by adding 200 mM sodium carbonate solution in twice amount of the reaction liquid. One unit of activity represents the activity by which 1 µmol of glucose is liberated per minute.

3. Results

Figure 14:
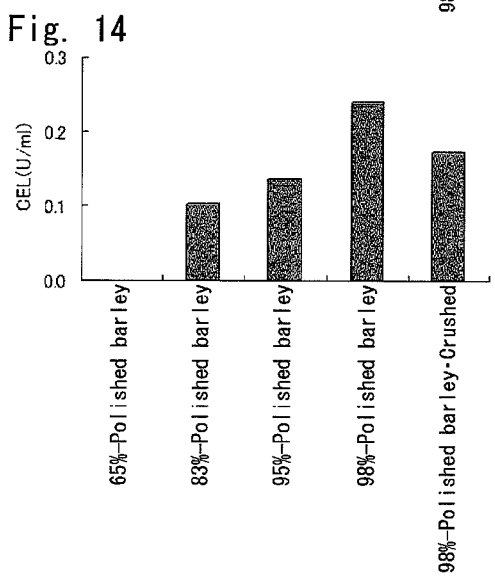
FIG. 14 shows cellulase (CEL) activities in *Aspergillus aculeatus* culture products using barley having various polishing ratios as culture raw material.
Figure 15:
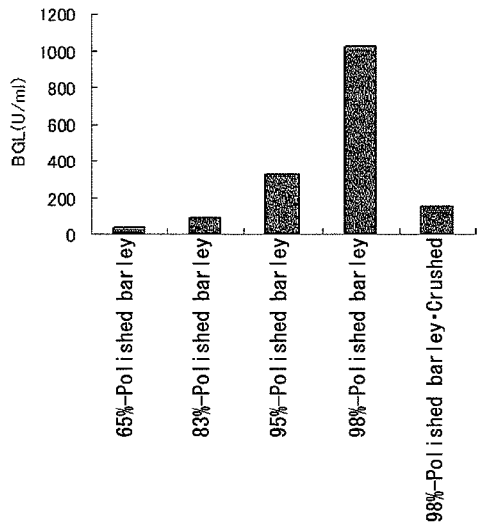
FIG. 15 shows β-glucosidase (BGL) activities in *Aspergillus aculeatus* culture products using barley having various polishing ratios as culture raw material.

FIGS. 14 and 15 show the measurement results. It was confirmed that productivity of plant fiber degradation enzyme was differed by the polishing ratio also in *Aspergillus aculeatus* that is a filamentous fungus except the koji molds. High enzymatic productivity was obtained when 98%-polished barley was used. However, the CEL and BGL activities decreased when the crushed product thereof was used. Thus, it was suggested that the nutrient release suppressing effect of barley husks on the release of nutrients contributes to the high production of those enzymes.

Example 7

Production of White Rot Fungus Culture Product Using Barley Having Various Polishing Ratios Culture products of a white rot fungus capable of producing cellulolytic enzymes were produced by using various degrees of polished barley (Stirling, made in Australia) by the method as described below, and enzymatic activities therein were measured.

1. Method of Culture (1) Method of Pre-Culture 100 ml of medium containing 2% of glucose, 0.5% of an yeast extract, 0.1% of potassium nitrate, 0.1% of monopotassium hydrogen phosphate, 0.07% of ammonium sulfate, 0.03% of magnesium sulfate heptahydrate, 0.02% of calcium chloride (every % is in w/vol) and water was put in a 500-ml baffled conical flask, and was sterilized at 121° C. for 15 minutes with autoclave to prepare a pre-culture medium. After cooling, the pre-culture medium was inoculated with 30 mycelial mats of 5 mm×5 mm in size of *Irpex lacteus* (*Irpex lacteus* NBRC5367), and cultured with shaking at 28° C. and 120 rpm for 96 hours to obtain a pre-culture liquid.

(2) Method of Main Culture 100 ml of medium containing 2% of polished barley, 0.1% of polypeptone, 0.14% of ammonium sulfate, 0.2% of potassium dihydrogen phosphate, 0.03% of urea, 0.03% of magnesium sulfate heptahydrate, 0.03% of calcium chloride, 0.1% of Tween 80 (every % is in w/vol) and water was put in a 500-ml baffled conical flask, and was sterilized at 121° C. for 15 minutes with autoclave to obtain a main culture medium.

65%-polished barley, 83%-polished barley, 98%-polished barley or a 98%-polished barley crushed product was used as the above-mentioned polished barley.

After cooling, the main culture medium was inoculated with 10 ml of the pre-culture liquid, and cultured with shaking at 28° C. and 120 rpm for 96 hours.

2. Method of Measuring Enzymatic Activity

After the culture was completed, the culture liquid was centrifuged to collect a supernatant, and activities of plant fiber degradation enzymes in the supernatant were measured.

(1) Method of Measuring Cellulase Activity

The cellulase (CEL) activity was measured by the method that amount of the reduced saccharide which is generated from hydrolysis of carboxymethylcellulose (CMC) as substrate was quantitated by the dinitrosalicylic acid (DNS) method. To be more specific, 1 ml of the culture liquid was added to 1 ml of 1% CMC substrate solution (a solution obtained by dissolving low Viscosity™ produced by Sigma-Aldrich in a 100 mM acetic acid buffer liquid (pH 5)), and enzymatic reaction was allowed to proceed at 40° C. exactly for 10 minutes. After that, 4 ml of the DNS reagent containing 0.75% of dinitrosalicylic acid, 1.2% of sodium hydroxide, 22.5% of potassium sodium tartrate tetrahydrate and 0.3% of lactose monohydrate, was added to the mixture, and well mixed to terminate the reaction. In order to quantitate the amount of reduced saccharide in the liquid after terminating the reaction, the liquid after terminating the reaction was heated in boiling water bath exactly for 15 minutes. Subsequently, the liquid was cooled to room temperature, absorbance at 540 nm was determined to quantitate amount of the reduced saccharide corresponding to that of glucose. One unit of cellulase (CEL) activity represents the amount of enzyme required for producing reduced saccharide which corresponds to 1 µmol of glucose per minute.

(2) Method of Measuring Xylanase Activity

Next, the xylanase (XYL) activity was measured by allowing the reduced saccharide which is generated by enzymatic hydrolysis of xylan derived from oat spelts as substrate to react with DNS, and quantitating the increase of absorbance at 540 nm. To be more specific, 0.1 ml of the culture liquid was added to 1.9 ml of 1% xylan substrate solution (xylan, from oat spelts produced by Sigma-Aldrich dissolved in a 200 mM acetic acid buffer liquid (pH 4.5)), and enzymatic reaction was allowed to proceed at 40° C. exactly for 10 minutes. After that, 4 ml of the DNS reagent containing 0.75% of dinitrosalicylic acid, 1.2% of sodium hydroxide, 22.5% of potassium sodium tartrate tetrahydrate, and 0.3% of lactose monohydrate, was added to the mixture, and well mixed to terminate the reaction. In order to quantitate the amount of reduced saccharide in the liquid after terminating the reaction, the liquid after terminating the reaction was heated in boiling water bath exactly for 15 minutes. Subsequently, the liquid was cooled to room temperature, absorbance at 540 nm was determined to quantitate amount of the reduced saccharide corresponding to that of xylose. One unit of xylanase activity represents the amount of enzyme required for producing reduced saccharide which corresponds to 1 µmol of xylose per minute under the reaction condition of 40° C. and 10 minutes.

3. Results

Figure 16:
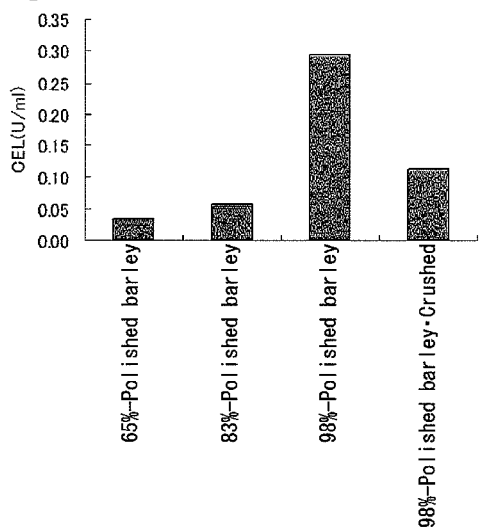
FIG. 16 shows cellulase (CEL) activities in white rot fungus culture products using barley having various polishing ratios as culture raw material.
Figure 17:
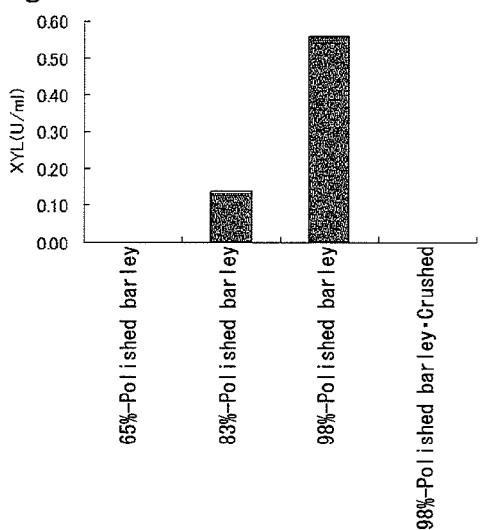
FIG. 17 shows xylanase (XYL) activities in white rot fungus culture products using barley having various polishing ratios as culture raw material.

FIGS. 16 and 17 show the measurement results. It was confirmed that productivity of plant fiber degradation enzyme was differed by the polishing ratio also in the white rot fungus. The highest enzymatic productivity was obtained when the 98%-polished barley was used. However, the enzymatic activity significantly decreased when the crushed product thereof was used. Thus, it was suggested that the nutrient release suppressing effect of barley husks on the release of nutrients contributes to the high production of the plant fiber degradation enzymes.

Example 8

Production of White Koji Mold Culture Product Using Pearled Barley which is not Gelatinized (1) Method of pre-culture: 8 g of pearled barley (Stirling, made in Australia) and 100 ml of water were put in a 500-ml baffled conical flask, and was sterilized at 121° C. for 15 minutes with autoclave to obtain a pre-culture medium. A white koji mold (*Aspergillus kawachii* NBRC4308) was inoculated at 1×10$^6$/ml into the pre-culture medium and cultured with shaking at 37° C. and 100 rpm for 24 hours to obtain a pre-culture liquid.

(2) Method of main culture: 0.2 g of $KNO_3$, 0.3 g of $KH_2PO_4$, and 100 ml of water were put in a 500-ml baffled conical flask, and was sterilized at 121° C. for 15 minutes with autoclave. After cooling, the chloramphenicol (Wako Pure Chemical Industries Co., Ltd.) was added to the resultant so as to be a concentration of 50 µg/ml, and 2 g of pearled barley which had not been treated by heat was added thereto to obtain a main culture medium. The main culture medium was inoculated with 1 ml of the pre-culture liquid, and cultured with shaking at 37° C. and 100 rpm for 72 hours to obtain koji mold culture product.

For control, koji mold culture product was produced by using gelatinized culture raw material. That is, 2 g of pearled barley, 0.2 g of $KNO_3$, 0.3 g of $KH_2PO_4$ and 100 ml of water were put in a 500-ml baffled conical flask, and was sterilized at 121° C. for 15 minutes with autoclave. After cooling, the chloramphenicol was added to the resultant so as to be a concentration of 50 µg/ml to obtain a main culture medium. The main culture medium was inoculated with 1 ml of the pre-culture liquid and cultured with shaking at 37° C. and 100 rpm for 72 hours to obtain koji mold culture product.

(3) Method of Measurement

Activities of glucoamylase, acid-stable α-amylase, and α-amylase in koji mold culture products obtained in respective experimental plots were measured. That is, the glucoamylase activity was measured by using a saccharification power fractional quantification kit (manufactured by Kikkoman Corporation). For measuring the acid-stable α-amylase activity, the method described in Sudo S. et al: J. Ferment. Bioeng., 76, 105-110 (1993), Sudo S. et al: J. Ferment. Bioeng., 77, 483-489 (1994), and Shigetoshi Sudo et al: Journal of the Brewing Society of Japan, 89, 768-774 (1994) was slightly modified. That is, acid-unstable α-amylase activity was inactivated by treating the culture product with acid, and then acid-stable α-amylase activity was measured with an α-amylase measurement kit (manufactured by Kikkoman Corporation). To be more specific, 9 ml of 100 mM acetic acid buffer liquid (pH 3) was added to 1 ml of culture liquid, and acid treatment was conducted at 37° C. for 1 hour, and measured with the α-amylase measurement kit (manufactured by Kikkoman Corporation). The α-amylase activity was measured by using an α-amylase measurement kit (manufactured by Kikkoman Corporation). The results are shown in Table 1.

(4) Results

In the pearled raw barley koji mold culture product of the present invention, both the glucoamylase and acid-stable α-amylase were produced in a good and balanced manner. The yield of α-amylase was whereas slightly low.

In the control, relatively large amounts of acid-stable α-amylase and α-amylase were produced. It is probably because the nutrient condition was maintained within a suitable range owing to the presence of $KNO_3$ and $KH_2PO_4$ although the gelatinized raw material was used.

Thus, it was revealed that koji mold culture product usable for producing fermented foods and drinks is produced according to the present invention.

TABLE 1

| | Experimental plot | |
| --- | --- | --- |
| Enzymatic activity | Pearled raw barley koji mold culture product (without husks and not gelatinized) | Control (without husks and gelatinized) |
| Glucoamylase activity (U/ml) | 110.6 | 29.2 |
| Acid-stable α-amylase activity (U/ml) | 3.6 | 3.7 |
| α-amylase activity (U/ml) | 8.3 | 10.7 |

Example 9

Production of Barley Shochu with White Koji Mold Culture Product by Using Pearled Barley which is not Gelatinized (1) Method of pre-culture: 8 g of pearled barley (Stirling, made in Australia) and 100 ml of water were put in a 500-ml baffled conical flask, and was sterilized at 121° C. for 15 minutes with autoclave to obtain a pre-culture medium. A white koji mold (*Aspergillus kawachii* NBRC4308) was inoculated at 1×10$^6$/ml into the pre-culture medium and cultured with shaking at 37° C. and 100 rpm for 24 hours to obtain a pre-culture liquid.

(2) Method of main culture: 0.5 g of pearled barley, 0.2 g of $KNO_3$, 0.3 g of $KH_2PO_4$ and 100 ml of water were put in a 500-ml baffled conical flask, and was sterilized at 121° C. for 15 minutes with autoclave to obtain a main culture medium. The main culture medium was inoculated with 1 ml of the pre-culture liquid, and cultured with shaking at 37° C. and 100 rpm for 24 hours. After that, 1.5 g of the pearled barley which had not been heat treated was added thereto, and cultured with shaking at 37° C. and 100 rpm for additional 48 hours to obtain koji mold culture product.

(3) Yeast: Kagoshima yeast was cultured with shaking overnight at 100 rpm in 1 ml of the YPD medium, centrifuged to collect cells, and washed twice with sterilized water.

(4) Mashing: Mashing combination was as shown in Table 2. For additional barley, the pearled barley that was washed, followed by 60-minute immersion, 30-minute drainage and 40-minute steaming, was used. Total amount of the above-mentioned yeast was used.

TABLE 2

|  | Primary | Secondary | Total |
|---|---|---|---|
| Additional barley (g) | 310 | 615 | 925 |
| Mashing water (ml) | 300 | 650 | 950 |
| Koji mold culture product (ml) | 350 | 0 | 350 |
| 90% lactic acid (ml) | 2 | 0 | 2 |

(5) Fermentation condition: Fermentation was conducted at 25° C. for 20 days. Secondary mashing was conducted 3 days after the primary mashing.

(6) Distillation: Distillation was conducted under a reduced pressure of −650 mmHg.

(7) Results

The fermentation successively proceeded, and the mash after the fermentation was completed had an alcohol content of 17.5%.

The sample obtained after distillation was organoleptically evaluated by the panels of 6 specialists in alcohol beverages. As a result, the obtained sample was highly evaluated with fine quality for alcohol beverages.

From the results, it was revealed that barley shochu having a quality without any defect was produced according to the method of the present invention.

Example 10

Production of Yellow Koji Mold Culture Product Using Pearled Barley which is not Gelatinized (1) Method of pre-culture: 8 g of pearled barley (Stirling, made in Australia) and 100 ml of water were put in a 500-ml baffled conical flask, and was sterilized at 121° C. for 15 minutes with autoclave to obtain a pre-culture medium. A yellow koji mold (*Aspergillus oryzaei* NRIB40) was inoculated at $1 \times 10^6$/ml into the pre-culture medium and cultured with shaking at 37° C. and 100 rpm for 24 hours to obtain a pre-culture liquid.

(2) Method of main culture: 0.8 g of $KNO_3$, 1.2 g of $KH_2PO_4$, 0.2 g of $MgSO_4$, and 100 ml of water were put in a 500-ml baffled conical flask, and was sterilized at 121° C. for 15 minutes with autoclave. After cooling, the chloramphenicol (Wako Pure Chemical Industries Co., Ltd.) was added to the resultant so as to be a concentration of 50 μg/ml, and 2 g of pearled barley was added thereto to obtain a main culture medium. The main culture medium was inoculated with 1 ml of the pre-culture liquid, and cultured with shaking at 37° C. and 100 rpm for 72 hours to produce a koji mold culture product.

For positive control, koji mold culture product was produced by the method according to the second aspect of the present invention. That is, 2 g of 95%-polished barley (Stirling, made in Australia), 0.8 g of $KNO_3$, 1.2 g of $KH_2PO_4$, 0.2 g of $MgSO_4$ and 100 ml of water were put in a 500-ml baffled conical flask, and was sterilized at 121° C. for 15 minutes with autoclave. After cooling, the chloramphenicol was added to the resultant so as to be a concentration of 50 μg/ml to obtain a main culture medium. The main culture medium was inoculated with 1 ml of the pre-culture liquid, and cultured with shaking at 37° C. and 100 rpm for 72 hours to produce a koji mold culture product.

(3) Results

Activities of glucoamylase and α-amylase in the koji mold culture products obtained in the respective experimental plots were measured in the same manner as in Example 8. Table 3 shows the results.

In the pearled raw barley koji mold culture products, glucoamylase was produced in a good manner, while the α-amylase activity was slightly low. The activities of both enzymes were inferior to those in the positive control. However, both enzymes were produced in a balanced manner. Thus, it was revealed that a koji mold culture product usable for producing fermented foods and drinks is provided.

TABLE 3

| | Experimental plot | |
|---|---|---|
| Enzymatic activity | Pearled raw barley koji mold culture product (without husks and not gelatinized) | Positive control (with husks and gelatinized) |
| Glucoamylase activity (U/ml) | 37.8 | 96.2 |
| α-amylase activity (U/ml) | 174.7 | 437.4 |

Experimental Example 2

Measurement of Glucose Liberation Rate in Barley Substrate Solutions Having Various Inorganic Salt Concentrations as Sterilized.

Barley substrate solutions were obtained by sterilizing with autoclave inorganic salt aqueous solutions of various salt concentrations which contain barley. Each of the barley substrate solutions was allowed to react with enzymes derived from koji mold culture product, and the glucose liberation rates from barley were measured.

1. Method of Preparing Barley Substrate Solution

First, 2 g of 98%-polished barley (Stirling, made in Australia) was weighed and then put in a 500-ml conical flask together with 50 ml of water. This was sterilized with autoclave (at 121° C. for 15 minutes) to prepare a barley substrate solution, which was then represented as "No. 1: control plot".

In "No. 2: plot with use of salts", the autoclave sterilization was conducted in the same manner as in the "No. 1: control plot" except that 50 ml of the inorganic salt aqueous solution containing 0.1 g of potassium nitrate and 0.15 g of potassium dihydrogen phosphate was used instead of water. In other words, the salts concentration as sterilized with autoclave was 0.2% of potassium nitrate and 0.3% of potassium dihydrogen phosphate.

In "No. 3: plot with use of salts at high concentrations as sterilized", the autoclave sterilization was conducted in the same manner as in "No. 1: control plot" except that 10 ml of an inorganic salt aqueous solution containing 0.1 g of potassium nitrate and 0.15 g of potassium dihydrogen phosphate was used instead of water, and that 40 ml of sterilized water was added thereto. In other words, the salts concentration as sterilized was 1.0% of potassium nitrate and 1.5% of potassium dihydrogen phosphate, which were 5 folds of those in the experimental plot No. 2. However, the salts concentration after sterilization and addition of water, was adjusted so as to be 0.2% of potassium nitrate and 0.3% of potassium dihydrogen phosphate, which were the same as those in the experimental plot No. 2.

2. Method of Preparing Koji Mold Culture Supernatant

Subsequently, koji mold culture product produced by using barley (Stirling, made in Australia) as culture raw material was subjected to solid-liquid separation by filtration with filtering paper to obtain "koji molds culture supernatant".

The method of producing the koji mold culture product used in this experiment were as described below.

(1) Method of Pre-Culture 8 g of 65%-polished barley and 100 ml of water were put in a 500-ml baffled conical flask, and was sterilized at 121° C. for 15 minutes with autoclave to obtain a pre-culture medium. After cooling, a white koji mold (Aspergillus kawachii NBRC4308) was inoculated at 1×10$^6$/ml into the pre-culture medium and cultured with shaking at 37° C. and 100 rpm for 24 hours to obtain a pre-culture liquid.

(2) Method of Main Culture

98%-polished barley was added to water supplemented with 0.2% (w/vol) of potassium nitrate and 0.3% (w/vol) of potassium dihydrogen phosphate so that the amount of 98%-polished barley was 2.0% (w/vol) to prepare liquid medium. 3,000 ml of the prepared liquid medium was put in a 5,000-ml jar fermentor (manufactured by B. E. Marubishi Co., Ltd.), and was sterilized with autoclave (at 121° C. for 15 minutes), followed by inoculating with 30 ml of the pre-culture liquid of the white koji mold (Aspergillus kawachii NBRC4308) pre-cultured in advance in the liquid medium by the above-mentioned method. After that, culture was conducted for 42 hours at a temperature of 37° C. and a stirring rate of 300 rpm and with an aeration volume of 0.5 vvm, and the resultant was filtrated with filtering paper (Toyo filter paper No. 2) to obtain "koji molds culture supernatant".

3. Method of Measuring Glucose Liberation Rate 50 ml of the barley substrate solution and 50 ml of the koji mold culture supernatant were separately kept at 37° C. for 5 minutes, and were then mixed to start reaction. Glucose concentrations in reaction liquids each sampled 3 hours after the initiation of the reaction were measured with Glucose C-II Test Wako (manufactured by Wako Pure Chemical Industries Co., Ltd.) to calculate the glucose liberation rates.

4. Results

Figure 18:
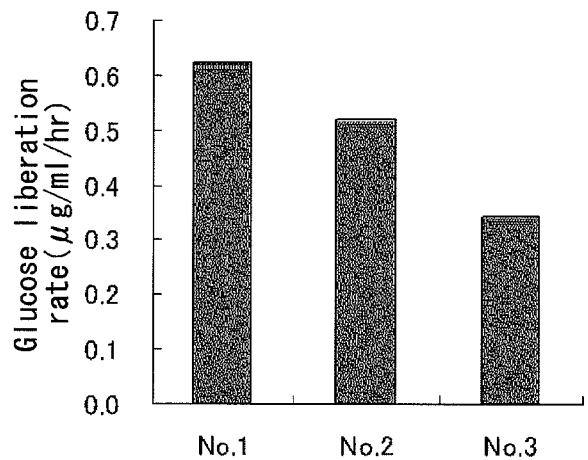
FIG. 18 shows glucose concentrations in reaction liquids obtained by allowing barley substrate solutions having various salt concentrations as sterilized to react with koji molds culture supernatant, respectively.

The glucose liberation rates calculated from the measurement results of glucose concentration in the reaction liquids were as shown in FIG. 18. It was confirmed that the glucose liberation rates were differed by the salt concentration upon preparation of the barley substrate solution. In Experimental Example 1, it was already shown that the glucose liberation rate was adjusted by polishing ratio of the barley. Experimental Example 2 also revealed that the glucose liberation rate becomes low by presence of the salts upon heat treatment such as autoclave sterilization. This was probably because the presence of salts as heat treated of the barley suppresses physical decomposition of the barley.

Example 11

Production of White Koji Mold Culture Products Using Barley Having Various Salt Concentrations as Sterilized White koji mold culture products were produced by using various degrees of polished barley (Stirling, made in Australia) by the method as described below, and enzymatic activities therein were measured.

1. Method of Pre-Culture 8 g of 65%-polished barley and 100 ml of water were put in a 500-ml baffled conical flask, and was sterilized at 121° C. for 15 minutes with autoclave to obtain a pre-culture medium. After cooling, a white koji mold (Aspergillus kawachii NBRC4308) was inoculated at 1×10$^6$/ml into the pre-culture medium and cultured with shaking at 37° C. and 100 rpm for 24 hours to obtain a pre-culture liquid.

2. Method of Main Culture 2 g of 98%-polished barley (Stirling, made in Australia) was weighed and then put in a 500-ml baffled conical flask together with 100 ml of water. This was sterilized at 121° C. for 15 minutes with autoclave to prepare a main culture medium, which was then represented as "No. 1: control plot".

In "No. 2: plot with use of salts", the autoclave sterilization was conducted in the same manner as in the "No. 1: control plot" except that 100 ml of the inorganic salt aqueous solution containing 0.2 g of potassium nitrate and 0.3 g of potassium dihydrogen phosphate was used instead of water.

In "No. 3: plot with use of salts at high concentrations as sterilized", the autoclave sterilization was conducted in the same manner as in "No. 1: control plot" except that 20 ml of an inorganic salt aqueous solution containing 0.2 g of potassium nitrate and 0.3 g of potassium dihydrogen phosphate was used instead of water, and that 80 ml of sterilized water was added thereto. In other words, the salts concentration as sterilized was 1.0% of potassium nitrate and 1.5% of potassium dihydrogen phosphate, respectively, which were 5 folds of those in the experimental plot No. 2. However, the salts concentration after sterilization and addition of water, was adjusted so as to be 0.2% of potassium nitrate and 0.3% of potassium dihydrogen phosphate, which were the same as those in the experimental plot No. 2.

After cooling, the thus-prepared main culture medium was inoculated with 1 ml of the pre-culture medium, and cultured with shaking at 37° C. and 100 rpm for 48 hours.

3. Method of Measurement

After the culture was completed, activities of glucoamylase (GA) and acid-stable α-amylase (ASAA), which are amylolytic enzymes, were measured.

The glucoamylase (GA) activity was measured by using a saccharification power fractional quantification kit (manufactured by Kikkoman Corporation).

For measuring the acid-stable α-amylase (ASAA) activity, the method described in Sudo S. et al: J. Ferment. Bioeng., 76, 105-110 (1993), Sudo S. et al: J. Ferment. Bioeng., 77, 483-489 (1994), and Shigetoshi Sudo et al: Journal of the Brewing Society of Japan, 89, 768-774 (1994) was slightly modified. That is, acid-unstable α-amylase activity was inactivated by treating the culture product with acid, and then acid-stable α-amylase activity was measured with an α-amylase measurement kit (manufactured by Kikkoman Corporation). To be more specific, 9 ml of 100 mM acetic acid buffer liquid (pH 3) was added to 1 ml of culture liquid, and acid treatment was conducted at 37° C. for 1 hour, and measured with the α-amylase measurement kit (manufactured by Kikkoman Corporation).

4. Results

Figure 19:
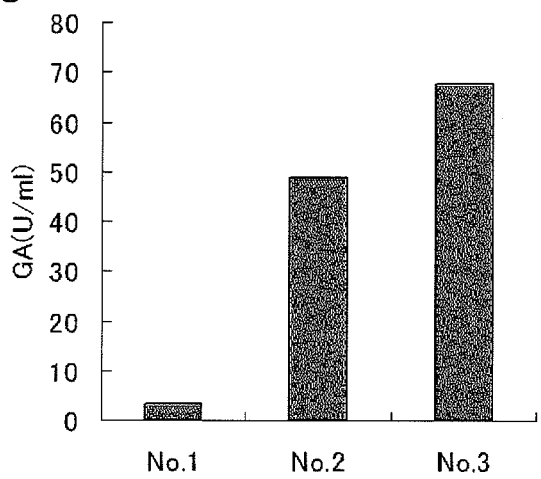
FIG. 19 shows glucoamylase (GA) activities in white koji mold culture products in which liquid media having various salt concentrations as sterilized were used.
Figure 20:
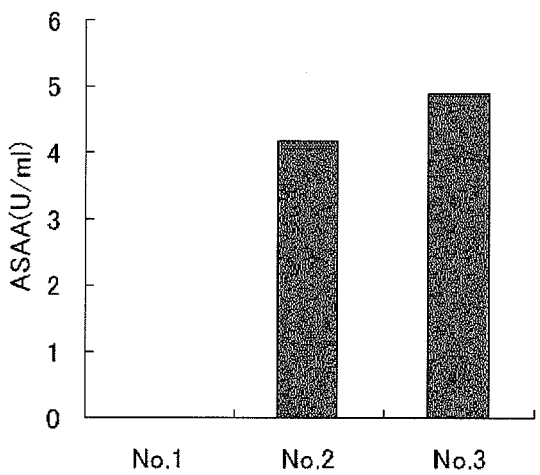
FIG. 20 shows acid-stable α-amylase (ASAA) activities in white koji mold culture products in which liquid media having various salt concentrations as sterilized were used.

FIG. 19 shows the measurement results of the glucoamylase activities, and FIG. 20 shows the measurement results of the acid-stable α-amylase activities.

As shown in FIGS. 19 and 20, the enzymatic productivity was improved in the plot No. 3 in which salts concentration as sterilized was high, as compared to that in the plot No. 2 which has the same salts concentration upon culturing. In Experimental Example 2, it was confirmed that the saccharide liberation rate from raw material barley became low as inorganic salt concentrations in a barley substrate solution as heat treated became high. Therefore, it was suggested that the enzymatic productivity is influenced by the saccharide liberation rate in addition to the effect of the salts on the growth of the koji mold. The plot No. 1 did not contain the salts, so it was thought that the growth of the koji mold was suppressed as well as the enzymatic production therein was significantly suppressed due to the high saccharide liberation rate.

Until now, the inorganic salts to be added as a medium is prepared were thought to be involved only in growth of koji molds during culture. According to this Example, however, there was suggested the possibility that the enzymatic production in liquid culture of koji molds is promoted also by the saccharide liberation suppressing effect from raw material barley.

INDUSTRIAL APPLICABILITY

According to the method of the present invention, nutrient concentration in the culture system is controlled to be low, so the culture mode equivalent to feeding culture is achieved by simple batch culture, without conducting feeding culture in which nutrients are added little by little from outside of the culture system.

According to the present invention, it is provided a method of stably and cheaply producing a filamentous fungus culture product for use in various industries in addition to for use in producing fermented foods and drinks, enzymes and an enzyme preparation which are produced from the filamentous fungus culture products.

Further, the present invention is expected to be applied to the heteroprotein production which uses promoter regions of an amylolytic enzyme gene and the like.

Thus, the present invention is applicable for a wide spectrum of industries comprising food manufacturing industry, fermentation industry, drug industry and the like.

The invention claimed is:

1. A method of producing filamentous fungi culture product comprising,
   culturing filamentous fungi in a liquid medium containing at least one culture raw material to increase production of enzymes in the filamentous fungus culture product, wherein
   the filamentous fungi is at least one selected from the group consisting of koji molds, fungi of genus *Aspergillus*, fungi of genus *Trichoderma*, and white rot fungi,
   the culture raw material comprises barley of which surface is entirely or partly covered with at least husks,
   the barley has a polishing ratio of more than 93%, and
   releasing rate of nutrients from the barley into the culture system is reduced by the husks to increase the production of enzymes.

2. The method of producing filamentous fungi culture product according to claim 1, wherein the barley is barley which is not gelatinized.

3. The method of producing filamentous fungi culture product according to claim 1,
   which comprises heat treating the liquid medium, and
   further reducing the releasing rate of nutrients from the barley into the liquid medium by increasing inorganic salt concentration in the liquid medium.

4. The method of producing filamentous fungi culture product according to claim 1, wherein the nutrients comprise saccharide derived from starch in the culture raw material and/or amino acid derived from protein in the culture raw material.

5. A method of producing filamentous fungi culture product according to claim 1, wherein the enzymes comprise at least one selected from the group consisting of amylolytic enzymes, plant fiber degradation enzymes and proteolytic enzymes.

* * * * *